United States Patent
del Alamo de Pedro et al.

(10) Patent No.: US 12,257,072 B2
(45) Date of Patent: Mar. 25, 2025

(54) MAPPING AND QUANTIFYING SHEAR STRESS AND HEMOLYSIS IN PATIENTS

(71) Applicants: The Regents of the University of California; Fundación para la Investigación Biomédica del Hospital Gregorio Marañó, Madrid (ES)

(72) Inventors: Juan Carlos del Alamo de Pedro, San Diego, CA (US); Lorenzo Rossini, San Diego, CA (US); Andrew Kahn, San Diego, CA (US); Javier Bermejo, Madrid (ES); Pablo Martínez-Legazpi, Madrid (ES); Raquel Yotti Alvarez, Madrid (ES)

(73) Assignee: The Regents of the University of California et al., Oakland, CA (US)

( * ) Notice: Subject to any disclaimer, the term of this patent is extended or adjusted under 35 U.S.C. 154(b) by 261 days.

(21) Appl. No.: 17/955,077

(22) Filed: Sep. 28, 2022

(65) Prior Publication Data
US 2023/0050982 A1  Feb. 16, 2023

Related U.S. Application Data

(63) Continuation of application No. 17/045,351, filed as application No. PCT/US2019/026146 on Apr. 5, 2019, now Pat. No. 11,471,101.
(Continued)

(51) Int. Cl.
*A61B 5/00* (2006.01)
*A61B 5/02* (2006.01)
(Continued)

(52) U.S. Cl.
CPC ........ *A61B 5/4851* (2013.01); *A61B 5/02035* (2013.01); *A61B 5/0263* (2013.01);
(Continued)

(58) Field of Classification Search
CPC ..... A61B 8/06; A61B 5/4851; A61B 5/02035; A61B 5/0263; A61B 5/0285;
(Continued)

(56) References Cited

U.S. PATENT DOCUMENTS 4,501,279 A 2/1985 Seo
10,716,519 B2 7/2020 del Alamo de Pedro et al.
(Continued)

FOREIGN PATENT DOCUMENTS

JP 2006/068524 3/2006
WO WO 2009/037484 3/2009
(Continued)

OTHER PUBLICATIONS

Benito Y, et al., Age-Dependence of Flow Homeostasis in the Left Ventricle. Front Physiol. Apr. 26, 2019;10:485. doi: 10.3389/fphys.2019.00485. PMID: 31105588; PMCID: PMC6498893 (Year: 2019).*
(Continued)

*Primary Examiner* — John D Li
(74) *Attorney, Agent, or Firm* — Fish & Richardson P.C.

(57) ABSTRACT

Provided herein are methods for in-vivo assessment of intraventricular flow shear stress, risk of hemolysis, also the location and extent of blood flow stasis regions and inside a cardiac chamber or blood vessel. Also provided herein are systems for performing such methods. Also provided herein are methods for assessing hemolysis and/or thrombosis risk in patients implanted with an LVAD. LVAD positioning and/or speed may be adjusted based on the results obtained by using methods described herein, and the risk for hemolysis and/or thrombosis can be minimized.

20 Claims, 11 Drawing Sheets

Related U.S. Application Data

(60) Provisional application No. 62/653,365, filed on Apr. 5, 2018, provisional application No. 62/653,389, filed on Apr. 5, 2018.

(51) Int. Cl.

| | |
|---|---|
| A61B 5/026 | (2006.01) |
| A61B 5/0285 | (2006.01) |
| A61B 5/055 | (2006.01) |
| A61B 8/00 | (2006.01) |
| A61B 8/06 | (2006.01) |
| A61B 8/08 | (2006.01) |
| A61M 60/178 | (2021.01) |
| A61M 60/857 | (2021.01) |
| G16H 30/40 | (2018.01) |
| G16H 50/30 | (2018.01) |

(52) U.S. Cl.
CPC ............ *A61B 5/0285* (2013.01); *A61B 5/055* (2013.01); *A61B 5/7225* (2013.01); *A61B 8/06* (2013.01); *A61B 8/065* (2013.01); *A61B 8/0883* (2013.01); *A61B 8/485* (2013.01); *A61B 8/488* (2013.01); *A61B 8/5223* (2013.01); *A61M 60/178* (2021.01); *A61M 60/857* (2021.01); *G16H 30/40* (2018.01); *G16H 50/30* (2018.01); *A61M 2205/04* (2013.01); *A61M 2250/00* (2013.01)

(58) Field of Classification Search
CPC ..... A61B 5/0555; A61B 5/7225; A61B 8/065; A61B 8/0883; A61B 8/485; A61B 8/488; A61B 8/5223; G01S 15/8984; G16H 30/40; G16H 30/30; G16H 50/30; A61M 60/178; A61M 60/857; A61M 2205/04; A61M 2250/00
See application file for complete search history.

(56) References Cited

U.S. PATENT DOCUMENTS

| | | |
|---|---|---|
| 11,471,101 B2 | 10/2022 | del Alamo de Pedro et al. |
| 11,771,379 B2 | 10/2023 | del Alamo de Pedro et al. |
| 2009/0253982 A1* | 10/2009 | Wang .................. A61B 5/4884 600/419 |
| 2011/0071382 A1 | 3/2011 | Miyazaki |
| 2011/0144967 A1 | 6/2011 | Adirovich |
| 2011/0257462 A1 | 10/2011 | Rodefeld |
| 2012/0078108 A1* | 3/2012 | Kim .................... A61B 8/5238 600/454 |
| 2012/0150516 A1 | 6/2012 | Taylor |
| 2012/0323118 A1 | 12/2012 | Menon Gopalakrishna et al. |
| 2013/0079610 A1 | 3/2013 | Al-Ali |
| 2014/0017718 A1* | 1/2014 | Tarasev .................. G01N 33/49 435/29 |
| 2014/0233814 A1 | 8/2014 | Ikeda et al. |
| 2014/0355863 A1 | 12/2014 | Xu et al. |
| 2015/0065847 A1 | 3/2015 | Choi et al. |
| 2015/0209498 A1 | 7/2015 | Franano et al. |
| 2015/0294461 A1* | 10/2015 | Satish ........................ G06T 7/90 382/128 |
| 2016/0140730 A1* | 5/2016 | Falahatpisheh ...... A61B 8/0883 382/128 |
| 2016/0210435 A1 | 7/2016 | Neumann |
| 2017/0087288 A1* | 3/2017 | Groß-Hardt ........ A61M 60/178 |
| 2017/0150928 A1 | 6/2017 | del Alamo de Pedro et al. |
| 2017/0232166 A1 | 8/2017 | Potenziano et al. |
| 2018/0031662 A1 | 2/2018 | Markl et al. |
| 2018/0045654 A1* | 2/2018 | Park ..................... G06V 20/695 |
| 2018/0364268 A1* | 12/2018 | Kluckner ............. G01B 11/245 |
| 2018/0372715 A1* | 12/2018 | Kluckner .............. G06T 7/0012 |
| 2019/0033230 A1* | 1/2019 | Kluckner ................ G06T 7/174 |
| 2019/0269379 A1* | 9/2019 | Kapoor .................. G16H 50/30 |
| 2020/0383644 A1 | 12/2020 | del Alamo de Pedro et al. |
| 2021/0145361 A1 | 5/2021 | del Alamo de Pedro et al. |
| 2021/0285868 A1* | 9/2021 | Jasperse ................. G01N 33/49 |

FOREIGN PATENT DOCUMENTS

| | | | |
|---|---|---|---|
| WO | WO 2014/107769 | 7/2014 | |
| WO | WO-2016133900 A1 * | 8/2016 | ............. G01J 3/462 |

OTHER PUBLICATIONS

Fraser et al., A quantitative comparison of mechanical blood damage parameters in rotary ventricular assist devices: shear stress, exposure time and hemolysis index. J Biomech Eng. Aug. 2012;134(8):081002. doi: 10.1115/1.4007092. PMID: 22938355; PMCID: PMC5413114 (Year: 2012).*

Rodriguez et al., "Intracardiac flow visualization: current status and future directions," European Heart Journal-Cardiovascular Imaging, Nov. 1, 2013, 14(11):1029-1038.

Abe et al., "Contrast echocardiography for assessing left ventricular vortex strength in heart failure: a prospective cohort study," European Heart Journal-Cardiovascular Imaging, Nov. 1, 2013, 14(11):1049-1060.

Arboix et al., "Cardioembolic stroke: clinical features, specific cardiac disorders and prognosis," Current cardiology reviews, Aug. 1, 2010, 6(3):150-161.

Auricchio et al., "Long-term clinical effect of hemodynamically optimized cardiac resynchronization therapy in patients with heart failure and ventricular conduction delay," Journal of the American College of Cardiology, Jun. 19, 2002, 39(12):2026-2033.

Bakalli et al., "Prevalence of left chamber cardiac thrombi in patients with dilated left ventricle at sinus rhythm: the role of transesophageal echocardiography," Journal of Clinical Ultrasound, Jan. 2013, 41(1): 8 Pages.

Benito et al., "Age-dependence of flow homeostasis in the left ventricle," Frontiers in physiology, Apr. 26, 2019, 10:1-12.

Benito et al., "Heart rate and AV delay modify left ventricular filling vortex properties," Circulation, 2012 126:A18099, 2 Pages.

Bermejo et al., "Diastolic chamber properties of the left ventricle assessed by global fitting of pressure-volume data: improving the gold standard of diastolic function," Journal of Applied Physiology, Aug. 15, 2013, 115(4):556-568.

Bermejo et al., "Intraventricular vortex properties in nonischemic dilated cardiomyopathy," American Journal of Physiology-Heart and Circulatory Physiology, Mar. 1, 2014, 306(5):H718-H729.

Bermejo et al., "The clinical assessment of intraventricular flows," Annual Review of Fluid Mechanics, Jan. 3, 2015, 47: 30 Pages.

Bluestein., "Research approaches for studying flow-induced thromboembolic complications in blood recirculating devices," Expert Rev Med Devices, 2004, 1(1): 17 Pages.

Bolger et al., "Transit of blood flow through the human left ventricle mapped by cardiovascular magnetic resonance," Journal of Cardiovascular Magnetic Resonance, Jan. 1, 2007, 9(5):741-747.

Bristow et al., "Cardiac-resynchronization therapy with or without an implantable defibrillator in advanced chronic heart failure," New England Journal of Medicine, May 20, 2004, 350(21):2140-2150.

Busch et al., "Reconstruction of divergence-free velocity fields from cine 3D phase-contrast flow measurements," Magn Reson Med, Jan. 2013, 69: 200-210.

Chakraborty et al., "On the relationships between local vortex identification schemes," Journal of fluid mechanics, Jul. 1, 2005, 535:189-214.

Chan et al., "Reevaluation of the Harboe assay as a standardized method of assessment for the hemolytic performance of ventricular assist devices," Artificial organs, Aug. 2012, 36(8):724-730.

Chaturvedi et al., "Increased airway pressure and simulated branch pulmonary artery stenosis increase pulmonary regurgitation after repair of tetralogy of Fallot: real-time analysis with a conductance catheter technique," Circulation, Feb. 4, 1997, 95(3): 14 Pages.

(56) References Cited

OTHER PUBLICATIONS

Chivukula et al., "Left ventricular assist device inflow cannula angle and thrombosis risk," Circulation: Heart Failure, Apr. 2018, 11(4): 9 Pages.

Chorin., "The numerical solution of the Navier-Stokes equations for an incompressible fluid," Bull. Am. Math. Soc. 1967, 73: 928-931.

Cortina et al., "Noninvasive assessment of the right ventricular filling pressure gradient. Circulation." Aug. 28, 2007, 116(9):1015-1023.

Cowger et al., "The development of aortic insufficiency in left ventricular assist device-supported patients," Circulation: Heart Failure, Nov. 2010, (6):668-674.

Del Álamo et al., "Self-similar vortex clusters in the turbulent logarithmic region," Journal of Fluid Mechanics, Aug. 1, 2006, 561:329-358.

Devesa et al., "Prediction of intraventricular thrombosis by quantitative imaging of stasis: A pilot color-doppler study in patients with acute myocardial infarction," J Am Coll Cardiol, 2015, 65(10S), 1 Page.

Domenichini et al., "Intraventricular vortex flow changes in the infarcted left ventricle: numerical results in an idealised 3D shape," Computer Methods in Biomechanics and Biomedical Engineering, Feb. 1, 2011, 14(01):95-101.

EP Extended European Search Report in European Appln. No. 16869290.3, dated Jun. 11, 2019, 8 pages.

Eriksson et al., "Four-dimensional blood flow-specific markers of LV dysfunction in dilated cardiomyopathy," European Heart Journal-Cardiovascular Imaging, May 1, 2013, 14(5):417-424.

Eriksson et al., "Quantification of presystolic blood flow organization and energetics in the human left ventricle," American Journal of Physiology-Heart and Circulatory Physiology, Jun. 2011 300(6):H2135-H2141.

Eriksson et al., Semi-automatic quantification of 4D left ventricular blood flow, Journal of Cardiovascular Magnetic Resonance, Dec. 1, 2010, 12(1): 10 Pages.

Esmaily-Moghadam et al., "A non-discrete method for computation of residence time in fluid mechanics simulations," Physics of Fluids, Nov. 23, 2013, 25(11): 22 Pages.

Evans et al., "Ultrasonic colour Doppler imaging," Interface Focus, 2011, 1(4):490-452.

Faludi et al., "Left ventricular flow patterns in healthy subjects and patients with prosthetic mitral valves: an in vivo study using echocardiographic particle image velocimetry," The Journal of thoracic and cardiovascular surgery, Jun. 1, 2010, 139(6):1501-1510.

Farwell et al., "How many people with heart failure are appropriate for biventricular resynchronization?" European heart journal, Aug. 1, 2000, 21(15):1246-1250.

Fatkin et al., "Relations between left atrial appendage blood flow velocity, spontaneous echocardiographic contrast and thromboembolic risk in vivo," Journal of American College of Cardiology, Mar. 1994, 23(4):961-969.

Flores et al., "Vorticity organization in the outer layer of turbulent channels with disturbed walls," Journal of Fluid Mechanics, Nov. 25, 2007, 591:145-154.

Fraser et al., "A quantitative comparison of mechanical blood damage parameters in rotary ventricular assist devices: shear stress, exposure time and hemolysis index, "Journal of biomechanical engineering, Aug. 1, 2012 134(8): 11 Pages.

Fredriksson et al., "4-D blood flow in the human right ventricle," American Journal of Physiology-Heart and Circulatory Physiology, Dec. 2011, 301(6):H2344-H2350.

Gao et al., "How to optimize intracardiac blood flow tracking by echocardiographic particle image velocimetry? Exploring the influence of data acquisition using computer-generated data sets," European Heart Journal-Cardiovascular Imaging, Jun. 1, 2012, 13(6):490-499.

Garcia et al., "Two-dimensional intraventricular flow mapping by digital processing conventional color-Doppler echocardiography images, " IEEE transactions on medical imaging, Jun. 17, 2010, 29(10):1701-1713.

García-Alvarez et al., "Noninvasive monitoring of serial changes in pulmonary vascular resistance and acute vasodilator testing using cardiac magnetic resonance," Journal of the American College of Cardiology, Oct. 22, 2013, 62(17):1621-1631.

Gardiner., "Handbook of stochastic methods for physics, chemistry, and the natural sciences," Berlin ; New York: Springer. 415 pages, 2004.

Gaschen et al., "Optimizing low velocity Doppler sonography in the abdomen," 26th Annual Forum of the American College of Veterinary Internal Medicine (ACVIM 2008), https://www.vin.com/apputil/conten/defaultadv1.aspx?pld=11262&id-3865707&print=1 (Year: 2008), 5 Pages.

Gharib et al., "Optimal vortex formation as an index of cardiac health," Proceedings of the National Academy of Sciences, Apr. 18, 2006, 103(16):6305-6308.

Goldberg et al., "Thirty-year trends (1975 to 2005) in the magnitude of, management of, and hospital death rates associated with cardiogenic shock in patients with acute myocardial infarction: a population-based perspective," Circulation, Mar. 2009, 119:1211-1219.

Goliasch et al., "CRT improves LV filling dynamics: insights from echocardiographic particle imaging velocimetry," JACC: Cardiovascular Imaging, Jun. 1, 2013, 6(6):704-713.

Gonzalez et al., "Automated axial right ventricle to left ventricle diameter ratio computation in computed tomography pulmonary angiography," PLoS One, May 22, 2015, 10(5): 14 Pages.

Goodwin et al., "Resolution of mitral regurgitation with left ventricular assist device support," The Annals of thoracic surgery, Sep. 1, 2017, 104(3):811-818.

Gorcsan et al., "Echocardiography for cardiac resynchronization therapy: recommendations for performance and reporting—a report from the American Society of Echocardiography Dyssynchrony Writing Group endorsed by the Heart Rhythm Society," Journal of the American Society of Echocardiography, Mar. 1, 2008, 21(3):191-213.

Guha et al., "Heart failure epidemiology: European perspective," Current cardiology reviews, May 1, 2013, 9(2):123-127.

Hellums JD, "1993 Whitaker Lecture: biorheology in thrombosis research. Annals of biomedical engineering," Sep. 1, 1994, 22(5):445-455.

Hendabadi et al., "Topology of blood transport in the human left ventricle by novel processing of Doppler echocardiography," Annals of biomedical engineering, Dec. 1, 2013, 41(12): 14 pages.

Homma et al., "Warfarin and aspirin in patients with heart failure and sinus rhythm," New England Journal of Medicine, May 17, 2012, 366(20):1859-1869.

Hong et al., "Characterization and quantification of vortex flow in the human left ventricle by contrast echocardiography using vector particle image velocimetry," JACC: Cardiovascular Imaging, Nov. 1, 2008, 1(6):705-717.

Hope et al., "Clinical evaluation of aortic coarctation with 4D flow MR imaging," Journal of Magnetic Resonance Imaging: An Official Journal of the International Society for Magnetic Resonance in Medicine, Mar. 2010, 31(3):711-718.

Jorde et al., "Prevalence, significance, and management of aortic insufficiency in continuous flow left ventricular assist device recipients," Circulation: Heart Failure, Mar. 2014, 7(2):310-319.

Jozsa et al., "Modelling Residence Time as Advection-Diffusion With Zero-Order Reaction Kinetics," Proceedings of the Hydroinformatics 2000 Conference, International Association of Hydraulic Engineering and Research, Jul. 2000, 7 Pages.

Kass, "Cardiac resynchronization therapy," Journal of cardiovascular electrophysiology, Sep. 2005, 16:S35-S41.

Kedia et al., "Usefulness of atrioventricular delay optimization using Doppler assessment of mitral inflow in patients undergoing cardiac resynchronization therapy," The American journal of cardiology, Sep. 15, 2006, 98(6):780-785.

(56) References Cited

OTHER PUBLICATIONS

Kerwin et al., "Ventricular contraction abnormalities in dilated cardiomyopathy: effect of biventricular pacing to correct interventricular dyssynchrony," Journal of the American College of Cardiology, Apr. 1, 2000, 35(5):1221-1227.
Kilner et al., "Asymmetric redirection of flow through the heart," Nature, Apr. 2000, 404(6779):759-761.
Kirklin et al., "Eighth annual INTERMACS report: special focus on framing the impact of adverse events," The Journal of Heart and Lung Transplantation, Oct. 1, 2017, 36(10):1080-1086.
Klotz et al., "Proposing a novel technique to exclude the left ventricle with an assist device: insights from 4-dimensional flow magnetic resonance imaging, " European Journal of Cardio-Thoracic Surgery, Sep. 1, 2016, 50(3):439-445.
Kormos, "Left ventricular assist device pump thrombosis: Understanding mechanisms as a key to causality," The Journal of thoracic and cardiovascular surgery, Dec. 2, 2014, 149(3):673-674.
Lang et al., "Recommendations for cardiac chamber quantification by echocardiography in adults: an update from the American Society of Echocardiography and the European Association of Cardiovascular Imaging," European Heart Journal-Cardiovascular Imaging, Mar. 1, 2015, 16(3):233-271.
Leonard et al., "The role of convection and diffusion on platelet adhesion and aggregation," Annals of the New York academy of sciences, Oct. 1972, 201(1):329-342.
Liao et al., "Ventricular flow dynamics with varying LVAD inflow cannula lengths: In-silico evaluation in a multiscale model," Journal of biomechanics, Apr. 27, 2018, 72: 26 Pages.
Lip et al., "Thromboembolism and antithrombotic therapy for heart failure in sinus rhythm," Thromb Haemost, 2012,108: 14 Pages.
Littmann et al., "Hemodynamic implications of left bundle branch block," Journal of electrocardiology, Jan. 1, 2000, 33:115-121.
Lowe, "Virchow's triad revisited: abnormal flow," Pathophysiology of haemostasis and thrombosis, 2003, 33(5-6):455-457.
Mangual et al., "Describing the highly three dimensional right ventricle flow," Annals of biomedical engineering, Aug. 1, 2012, 40(8):1790-1801.
Martínez-Legazpi et al., "Contribution of the diastolic vortex ring to left ventricular filling," Journal of the American College of Cardiology, Oct. 21, 2014, 64(16):1711-1721.
Martinez-Legazpi et al., "Stasis mapping using ultrasound: a prospective study in acute myocardial infarction," JACC: Cardiovascular Imaging, Mar. 5, 2018, 11(3):514-515.
Massie et al., "Randomized trial of warfarin, aspirin, and clopidogrel in patients with chronic heart failure: the Warfarin and Antiplatelet Therapy in Chronic Heart Failure (WATCH) trial," Mar. 31, 2009, 119(12):1616-1624.
May-Newman et al., "Thromboembolism is linked to intraventricular flow stasis in a patient supported with a left ventricle assist device," Asaio Journal, Jul. 1, 2013, 59(4):452-455.
Mehra et al., "A fully magnetically levitated circulatory pump for advanced heart failure," New England journal of medicine, Feb. 2, 2017, 376(5):440-450.
Mittal et al., "A versatile sharp interface immersed boundary method for incompressible flows with complex boundaries," Journal of computational physics, May 1, 2008, 227(10):4825-4852.
Mody et al., "Influence of Brownian motion on blood platelet flow behavior and adhesive dynamics near a planar wall, " Langmuir, May 22, 2007, 23(11):6321-6328.
O'Neill et al., "The current use of Impella 2.5 in acute myocardial infarction complicated by cardiogenic shock: results from the USpella Registry," Journal of interventional cardiology, Feb. 2014, 27(1):1-11.
Ouweneel et al., "Percutaneous Mechanical Circulatory Support Versus Intra-Aortic Balloon Pump in Cardiogenic Shock After Acute Myocardial Infarction," J Am Coll Cardiol, Jan. 24, 2017, 69(3):278-287.
Paul et al., "Shear stress related blood damage in laminar couette flow," Artificial organs, Jun. 2003, 27(6):517-529.

Pavlopoulos et al., "Recent advances in cardiac resynchronization therapy: echocardiographic modalities, patient selection, optimization, non-responders-all you need to know for more efficient CRT," The international journal of cardiovascular imaging, Feb. 1, 2010, 26(2):177-1791.
PCT International Preliminary Report on Patentability in International Appln. No. PCT/US2016/063626, mailed Jun. 7, 2018, 12 pages.
PCT International Preliminary Report on Patentability in International Appln. No. PCT/US2019/026146, dated Oct. 15, 2020, 9 pages.
PCT International Search Report and Written Opinion in Application No. PCT/US2016/063626, dated Feb. 2, 2017, 13 pages.
PCT International Search Report and Written Opinion in International Appln. No. PCT/US2019/026146, dated Jun. 20, 2019, 16 pages.
Pedrizzetti et al., "Changes in electrical activation modify the orientation of left ventricular flow momentum: novel observations using echocardiographic particle image velocimetry," European Heart Journal-Cardiovascular Imaging, Feb. 1, 2016, 17(2):203-209.
Pedrizzetti et al., "Left ventricular fluid mechanics: the long way from theoretical models to clinical applications," Annals of biomedical engineering, Jan. 1, 2015 43(1): 15 Pages.
Pedrizzetti et al., "Nature optimizes the swirling flow in the human left ventricle," Physical review letters, Sep. 2, 2005, 95(10): 4 Pages.
Pedrizzetti et al., "The vortex-an early predictor of cardiovascular outcome?" Nature Reviews Cardiology, Sep. 2014, 11(9): 9 Pages.
Pérez Del Villar et al., "The role of elastic restoring forces in right-ventricular filling," Cardiovascular research, Jul. 1, 2015, 107(1):45-55.
Perry et al., "A description of eddying motions and flow patterns using critical-point concepts," Annual Review of Fluid Mechanics, Jan. 1987, 19(1):125-155.
Platts et al., "Contrast microsphere destruction by a continuous flow ventricular assist device: an in vitro evaluation using a mock circulation loop," BioMed research international, Jan. 1, 2017, 2017: pp. 1-10.
Ponikowski et al.,"2016 ESC Guidelines for the diagnosis and treatment of acute and chronic heart failure," European Heart Journal, 37(27), 2129-2200.
Prisco et al., "Impact of LVAD implantation site on ventricular blood stagnation," ASAIO journal (American Society for Artificial Internal Organs; 1992), Jul. 2017, 63(4): 18 Pages.
Quaini et al., "Numerical characterization of hemodynamics conditions near aortic valve after implantation of left ventricular assist device," Mathematical Biosciences & Engineering, Jul. 1, 2011, 8(3):785-805.
Ramstack et al., "Shear-induced activation of platelets," Journal of biomechanics, Jan. 1, 1979, 12(2):113-125.
Reider et al., "Intraventricular thrombus formation in the LVAD-assisted heart studied in a mock circulatory loop," Meccanica, Feb. 1, 2017, 52(3): 14 Pages.
Richter et al., "Cardiology is flow," Circulation 113, 2006, (23):2679-2682.
Rodevand et al., "Diastolic flow pattern in the normal left ventricle," Journal of the American Society of Echocardiography, Jun. 1, 1999, 12(6):500-507.
Rogers et al., "Intrapericardial left ventricular assist device for advanced heart failure," New England Journal of Medicine, Feb. 2, 2017, 376(5):451-460.
Rossini et al., "A clinical method for mapping and quantifying blood stasis in the left ventricle," Journal of biomechanics, Jul. 26, 2016, 49(11): 10 Pages.
Rossini et al., "Clinical assessment of intraventricular blood transport in patients undergoing cardiac resynchronization therapy," Meccanica, Feb. 1, 2017, 52(3): 14 Pages.
Sawhney et al., "Randomized prospective trial of atrioventricular delay programming for cardiac resynchronization therapy," Heart rhythm, Nov. 1, 2004, 1(5):562-567.
Saxon et al., "Acute effects of intraoperative multisite ventricular pacing on left ventricular function and activation/contraction sequence

(56) References Cited

OTHER PUBLICATIONS in patients with depressed ventricular function," Journal of cardiovascular electrophysiology, Jan. 1998, 9(1):13-21.
Schinkel et al., "Safety and feasibility of contrast echocardiography for the evaluation of patients with HeartMate 3 left ventricular assist devices, " Eur Heart J Cardiovasc Imaging, Jun. 1, 2018, 19(6): 4 Pages.
Sengupta et al., "Emerging trends in CV flow visualization," JACC Cardiovasc Imaging, Mar. 2012, 5(3):305-316.
Seo et al., "A coupled chemo-fluidic computational model for thrombogenesis in infarcted left ventricles," American Journal of Physiology-Heart and Circulatory Physiology, Jun. 1, 2016, 310(11):H1567-H1582.
Seo et al., "Effect of diastolic flow patterns on the function of the left ventricle," Physics of Fluids, Nov. 23, 2013, 25(11): 22 Pages.
Shah et al., "Left ventricular assist device outcomes based on flow configuration and pre-operative left ventricular dimension: an interagency registry for mechanically assisted circulatory support analysis," The Journal of Heart and Lung Transplantation, Jun. 1, 2017, 36(6): 28 Pages.
Slaughter et al., "Advanced heart failure treated with continuous-flow left ventricular assist device," New England Journal of Medicine, Dec. 3, 2009, 361(23):2241-2251.
Smiseth et al., "A reproducible and stable model of acute ischaemic left ventricular failure in dogs," Clinical Physiology, Jun. 1982, 2(3):225-239.
Stanton et al., "How should we optimize cardiac resynchronization therapy?" European heart journal, Oct. 1, 2008, 29(20):2458-2472.
Tarbell, "Mass transport in arteries and the localization of atherosclerosis," Annual review of biomedical engineering, Aug. 2003, 5(1):79-118.
Therrien et al., "Impact of pulmonary valve replacement on arrhythmia propensity late after repair of tetralogy of Fallot," Circulation, May 22, 2001, 103(20):2489-2494.
Thiele et al., "Intraaortic balloon support for myocardial infarction with cardiogenic shock," New England Journal of Medicine, Oct. 4, 2012 367(14):1287-1296.
Thompson et al., "Fast measurement of intracardiac pressure differences with 2D breath-hold phase-contrast MRI. Magnetic Resonance in Medicine: An Official Journal of the International Society for Magnetic Resonance in Medicine," Jun. 2003, 49(6):1056-1066.
Toeg et al., "An update on mechanical circulatory support for heart failure therapy," Curr Opin Cardiol, Mar. 2014, 29(2):167-173.
Uejima et al., "A new echocardiographic method for identifying vortex flow in the left ventricle: numerical validation," Ultrasound Med Biol, May 2010, 36(5):772-788.
Vu et al., "Mitral valve prosthesis design affects hemodynamic stasis and shear in the dilated left ventricle," Annals of biomedical engineering, May 15, 2019, 47(5): 16 Pages.

Waggoner et al., "Left ventricular diastolic filling prior to cardiac resynchronization therapy: implications for atrioventricular delay programming," Pacing and clinical electrophysiology, Jul. 2008, 31(7):838-844.
Watanabe et al., "The looped heart does not save energy by maintaining the momentum of blood flowing in the ventricle," American Journal of Physiology-Heart and Circulatory Physiology, May 2008, 294(5):H2191-H2196.
Wigström et al., "Particle trace visualization of intracardiac flow using time-resolved 3D phase contrast MRI. Magnetic Resonance in Medicine: An Official Journal of the International Society for Magnetic Resonance in Medicine," Apr. 1999, 41(4):793-799.
Wong et al., "Intraventricular flow patterns and stasis in the LVAD-assisted heart," Journal of biomechanics, Apr. 11, 2014, 47(6):1485-1494.
Xiao et al., "Effects of abnormal activation on the time course of the left ventricular pressure pulse in dilated cardiomyopathy," Heart, Oct. 1, 1992, 68(10):403-407.
Xiao et al., "Natural history of abnormal conduction and its relation to prognosis in patients with dilated cardiomyopathy," International journal of cardiology, Feb. 1, 1996, 53(2):163-170.
Yancy et al., "2017 ACC/AHA/HFSA focused update of the 2013 ACCF/AHA guideline for the management of heart failure: a report of the American College of Cardiology/American Heart Association Task Force on Clinical Practice Guidelines and the Heart Failure Society of America," Journal of the American College of Cardiology, Jul. 31, 2017, 70(6):776-803.
Yang et al., "Flow and myocardial interaction: an imaging perspective." Philosophical Transactions of the Royal Society B: Biological Sciences, Aug. 29, 2007, 362(1484):1329-1341.
Yotti et al., "Doppler-Derived Ejection Intraventricular Pressure Gradients Provide a Reliable Assessment of Left Ventricular Systolic Chamber Function," Circulation, Sep. 20, 2005, 112(12):1771-1779.
Yotti et al., "Noninvasive estimation of the rate of relaxation by the analysis of intraventricular pressure gradients," Circulation: Cardiovascular Imaging, Mar. 2011, 4(2):94-104.
Zhang et al., "Assessment of left ventricular 2D flow pathlines during early diastole using spatial modulation of magnetization with polarity alternating velocity encoding: a study in normal volunteers and canine animals with myocardial infarction," Magnetic resonance in medicine, Sep. 2013, 70(3):766-775.
Zhang et al., "Different independent susceptibility markers for first-ever cerebral infarction and myocardial infarction in young patients," Journal of neurology, Jul. 1, 2012, 259(7):1420-1425.
Zhang et al., "The role of repeating optimization of atrioventricular interval during interim and long-term follow-up after cardiac resynchronization therapy," International journal of cardiology, Feb. 29, 2008, 124(2):211-217.
Zwanenburg et al., "Regional timing of myocardial shortening is related to prestretch from atrial contraction: assessment by high temporal resolution MRI tagging in humans," American Journal of Physiology-Heart and Circulatory Physiology, Feb. 2005, 288(2):H787-H794.

* cited by examiner

MAPPING AND QUANTIFYING SHEAR STRESS AND HEMOLYSIS IN PATIENTS

CROSS-REFERENCE TO RELATED APPLICATIONS

This application is a continuation of U.S. application Ser. No. 17/045,351, filed on Oct. 5, 2020, which claims the benefit of International Application No. PCT/US2019/026146, filed Apr. 5, 2019, which claims priority to U.S. Provisional Application Ser. No. 62/653,365 and U.S. Provisional Application Ser. No. 62/653,389, both filed on Apr. 5, 2018, the disclosures of which are herein incorporated by reference in their entireties.

FEDERALLY SPONSORED RESEARCH OR DEVELOPMENT

This invention was made with Government support under Grant No. 1R21 HL108268-01 awarded by the National Institutes of Health. The Government has certain rights in the invention.

TECHNICAL FIELD

Provided herein are methods for determining the presence of intracardiac thrombosis and/or hemolysis, or risks of thrombosis and/or hemolysis, in a patient (e.g., a patient having a LVAD) by assessing the location and extent of intraventricular blood dynamics inside a cardiac chamber.

BACKGROUND

Cardiovascular diseases are the leading cause of mortality worldwide and are projected to cause more than 20 million deaths per year by 2030. Cardiogenic shock remains the main cause of mortality in patients hospitalized for an acute myocardial infarction despite early revascularization (1). In this scenario, short-term mechanical circulatory support provides a crucial time span for the recovery of the stunned myocardium (2). Although the mortality of these patients is as high as 40% (3-5), hospital survivors have an excellent chance for long-term survival. Therefore, any improvement in short-term outcomes entails huge clinical impact.

In patients with advanced heart failure, refractory to medical therapy, treatment with left ventricular assist devices (LVADs) decreases mortality and improves quality of life. Therefore, these devices are increasingly being used, both as bridge therapy to cardiac transplantation and as destination therapy. Currently, there are a lack of clinical tools to guide optimal LVAD settings and cannula placement to improve outcomes and decrease complications. Ramp studies with standard echocardiographic views are sometimes used to choose pump speeds, but there are limited data showing the utility of this approach. Two important complications of LVAD therapy are hemolysis and thrombosis. Hemolysis is known to be associated with regions of high shear stress and thrombosis is associated with relative stasis, but currently the risks of these are difficult to estimate in clinical practice and therefore difficult to mitigate. Understanding the effects of an LVAD on intraventricular flow patterns and hemodynamics may help guide optimal pump settings, provide input on optimum cannula placement, decrease the rate of complications, and improve outcomes.

The normal LV flow pattern consists of a large diastolic vortex that channels the transit of blood towards the aortic valve. This vortex contributes to diastolic suction and minimizes kinetic energy losses and cardiac work (6, 7). In patients with LV systolic dysfunction, abnormal vortex structures are associated with greater energy dissipation and decreased pumping efficiency. These flow patterns drive complex fluid transport processes, whose impact on cardiovascular physiology and disease remains unexplored, especially in patients implanted with assist devices. Blood particles follow convoluted trajectories inside the LV (8-10). Intraventricular stasis and hemodynamic stresses are the cumulative result of the dynamical interactions between incoming flow and residual flow from preceding cycles (11). In the healthy heart, as a result of these processes there are minimal associated blood stasis and shear-induced hemolysis. However, intraventricular flow patterns can be significantly altered in cardiomyopathies (12-15), leading to increased blood stasis (14, 16). It has recently been shown that intraventricular cannula implantation and flow suction can also significantly alter these flow patterns in LVAD-implanted patients (17, 18). Likewise, biventricular pacemaker settings affect the efficiency of LV blood redirection (19).

Thus, it has been recognized that a deeper understanding of LV blood flow dynamics in normal and diseased LVs, may enhance the current characterization of cardiac physiology and lead to a better knowledge of the pathophysiology of HF, facilitate subclinical diagnosis of cardiac diseases, improve tools used for characterizing, predict risk of thrombus formation and guide treatment strategies. With the use of the current generation of continuous-flow assistances, the natural blood flow path through the heart is necessarily disrupted to some degree. Proper positioning and speed adjustment of these devices provide an optimal flow and minimize hemolysis related to shear stress blood damage (17, 20). Also, the decrease of the natural flow pulsatility accompanying continuous flow support may exacerbate the mixing of blood, decreasing intraventricular washout and potentially increasing cardioembolic risk.

SUMMARY

In some embodiments, novel echocardiographic modalities to map blood flow velocity inside the LV and its changes during the cardiac cycle are provided herein. In some embodiments, novel echocardiographic modalities provided herein include 2D echo color Doppler velocimetry (echo-CDV). In some embodiments, novel echocardiographic modalities provided herein allow for non-invasive personalized risk assessment of hemolysis and blood clot formation inside the left ventricle.

In some embodiments, obtaining flow-velocity images of blood inside a cardiac chamber or blood vessel (e.g. a cardiac chamber or blood vessel in a subject having a LVAD) is performed using a medical image-based apparatus able to determine blood flow velocity field. For example, the medical image-based apparatus can be an echocardiogram apparatus, a magnetic resonance imaging (MRI) apparatus, an echocardiographic imaging apparatus, a 2D color-Doppler velocimetry (echo-CDV) apparatus, an echo-particle-image-velocimetry (echo-PIV) apparatus, a synthetic aperture ultrasound apparatus or a transverse oscillation ultrasound vector velocimetry apparatus, or other medical image-based apparatus known to the skilled artisan. In some embodiments, flow-velocity images obtained from the medical image-based apparatus and suitable for the methods described herein include one, two, or three-dimensional images resolved in time.

In some aspects, provided herein are methods for characterizing vortex patterns inside a cardiac chamber or blood vessel of a subject (e.g., a subject having a LVAD) comprising obtaining flow-velocity images of blood inside a cardiac chamber or blood vessel of a subject, calculating the flow vorticity, ω, which will be used to characterize the flow structures by tracking flow patterns in time. The flow structures can be characterized by their circulation, kinetic energy, radius, aspect ratio, and the trajectory of their center.

In some aspects, provided herein are methods for assessing the risk of cumulative blood shear stress and hemolysis comprising calculating the plasma free hemoglobin, total hemoglobin the blood, cumulative fluid shear stress, and residence time (TR) (e.g., in a subject having a LVAD). The region of highest cumulative shear corresponds with the boundary of the LV vortex.

In some aspects, provided herein are methods for identifying regions of blood flow stasis inside a cardiac chamber or blood vessel of a subject (e.g., a subject having a LVAD) comprising obtaining flow-velocity images of blood inside a cardiac chamber or blood vessel of the subject, calculating the residence time (TR), the standard deviation of the residence time (σ_R), kinetic energy, and/or rate of distortion of blood particles inside the cardiac chamber or blood vessel using the flow-velocity images to generate numerical metrics of blood flow, and generating residence time (TR), kinetic energy, and/or rate of distortion maps using the numerical metrics to identify and characterize regions of blood flow stasis. Further, the disclosure provides a method to systematically analyze the effect of LVAD support on LV filling transport where low K (kinetic energy) or/and high Ts are indicators of blood stasis.

The cardiac chamber or blood vessel can be any cardiac chamber or blood vessel in which the blood velocity can be resolved. For example, the cardiac chamber can be the left ventricular chamber, left atrium chamber, left atrial appendage, right-ventricular chamber, or right atrium chamber. In some embodiments, regions of blood flow stasis are determined by calculating the residence time (TR), the standard deviation of the residence time (σ_R), kinetic energy, and/or rate of distortion of blood particles in more than one cardiac chamber or blood vessel (e.g., 2, 3, 4, 5, or more cardiac chambers or blood vessels).

In some embodiments, calculating the residence time (TR) of blood particles includes utilizing the equation:

$$(\partial_t T_R)/\partial t + \nabla \cdot (\vec{v} \, T_R) = 1$$

In some embodiments, the disclosure provides methods to calculate pressure maps from flow velocity data from medical images.

In some embodiments, in patients with LVADs, the numerical metrics of blood flow are additionally used to map the size and/or location of blood transport structures that transit from and/or into device flow elements such as inflow and/or outflow cannulas. The normalized orientation of the cannula may be used to parameterize cannula positioning. The orientation of the cannula with respect to flow structures may be a relevant parameter that dictates shear stresses, residence time, etc.

In some embodiments, provided herein are methods for identifying a region of hemolysis inside a cardiac chamber or blood vessel of a subject having a LVAD that include: obtaining flow-velocity images of blood inside a cardiac chamber or blood vessel of the subject; calculating hemolysis using the flow-velocity images using the following equation:

$$\frac{\Delta PfHb}{Hb} = C \sum{}^a T_R^{b-1}$$

wherein PfHb is the plasma free hemoglobin, Hb is the total hemoglobin in the blood (intracellular and extracellular), Σ is the cumulative fluid shear stress experienced by blood particles in seconds−1, TR is the residence time of the blood particles in seconds, and a, b, and c are empirical constants; wherein Σ is determined using the forced transport equation:

$$\frac{D\sum}{Dt} = \partial_t \sum + \nabla \cdot \left(v \sum\right) = S,$$

$$\sum(x, t = 0) = 0,$$

$$\sum(x_{inlet}, t) = 0,$$

wherein S is the Von-Mises stress at each point of space and time inside the left ventricle, and wherein S is determined from a velocity field obtained from the flow velocity images.

In some embodiments, provided herein are methods for evaluating an intraventricular region of hemolysis inside a cardiac chamber or blood vessel of a first subject that include: implanting a left ventricular assist device (LVAD) into the first subject at a first location, wherein the LVAD operates under a first set of operating parameters; obtaining flow-velocity images of blood inside a cardiac chamber or blood vessel of the first subject; calculating hemolysis using the flow-velocity images using the following equation:

$$\frac{\Delta PfHb}{Hb} = C \sum{}^a T_R^{b-1}$$

wherein PfHb is the plasma free hemoglobin, Hb is the total hemoglobin in the blood (intracellular and extracellular), Σ is the cumulative fluid shear stress experienced by blood particles in seconds−1, TR is the residence time of the blood particles in seconds, and a, b, and c are empirical constants; wherein Σ is determined using the forced transport equation:

$$\frac{D\sum}{Dt} = \partial_t \sum + \nabla \cdot \left(v \sum\right) = S,$$

$$\sum(x, t = 0) = 0,$$

$$\sum(x_{inlet}, t) = 0,$$

wherein S is the Von-Mises stress at each point of space and time inside the left ventricle, and wherein S is determined from a velocity field obtained from the flow-velocity images.

In some embodiments, methods provided herein include calculating one or more of residence time (TR), standard deviation of residence time (σTR), inside the cardiac chamber or blood vessel using the flow-velocity images to generate numerical metrics of blood flow; and calculating one or more of cumulative von-Mises stress map (Σ), standard deviation of residence von-Mises stress (σΣ), inside the cardiac chamber or blood vessel using the flow velocity images to generate numerical metrics of blood flow; or combinations thereof, using the numerical metrics to identify and characterize regions of hemolysis. In some embodiments, generating numerical metrics of blood flow comprises calculating the plasma free hemoglobin (PfHb) inside the cardiac chamber or blood vessel, and the standard deviation of plasma free hemoglobin (σPfHb). In some embodiments, calculating the standard deviation of plasma free hemoglobin (σPfHb) in regions with high blood plasma free hemoglobin (PfHb) inside the cardiac chamber or blood vessel. In some embodiments, generating numerical metrics of blood flow comprises calculating the rate of distortion of blood flow inside any cardiac chamber or blood vessel. In some embodiments, calculating the blood flow's rate of distortion in regions with high blood plasma free hemoglobin (PfHb) inside the cardiac chamber or blood vessel. In some embodiments, generating numerical metrics of blood flow comprises calculating the size, shape, mobility, distance to the chamber wall, and perimeter in contact with the chamber wall of regions with high blood plasma free hemoglobin (PfHb).

In some embodiments, the cardiac chamber is any cardiac chamber or blood vessel in which the blood velocity can be resolved. In some embodiments, the cardiac chamber is the left ventricular chamber, left atrium chamber, left atrial appendage, right-ventricular chamber, or right atrium chamber.

In some embodiments, obtaining flow-velocity images of blood inside a cardiac chamber or blood vessel is performed using a medical image based apparatus able to determine blood flow velocity field. In some embodiments, the medical image-based apparatus is an echocardiogram apparatus, a magnetic resonance imaging (MM) apparatus, an echocardiographic imaging apparatus, a 2D color-Doppler velocimetry (echo-CDV) apparatus, an echo-PIV apparatus, a synthetic aperture ultrasound apparatus, or a transverse oscillation ultrasound vector velocimetry apparatus. In some embodiments, the flow-velocity images comprise one, two, or three-dimensional images resolved in time. In some embodiments, multiple flow-velocity images are obtained using different velocity scales, and wherein data from the obtained flow velocity images are retrospectively merged to generate a flow map, a residence time (TR) map, a cumulative von-Mises stress map (Σ), a rate of distortion map, or combinations thereof. In some embodiments, calculating the residence time (TR) of blood particles comprises utilizing the equation:

$$\frac{\partial T_R}{\partial t} + \nabla \cdot (\vec{v} T_R) = 1.$$

In some embodiments, the standard deviation of Σ is caused by noise in the velocity measurements, and wherein calculating the standard deviation of Σ comprises utilizing the equation:

$$\sigma_\Sigma(x, t) = \sqrt{S_\Sigma(x,t) - \Sigma^2(x,t)}$$

wherein SΣ and Σ obey the equations:

$$\frac{\partial \Sigma}{\partial t} + \nabla \cdot (\vec{v}\Sigma) = S + \nabla \cdot (k\nabla \Sigma)$$

$$\frac{\partial S_\Sigma}{\partial t} + \nabla \cdot (\vec{v} S_\Sigma) = 2\Sigma + \nabla \cdot (k\nabla S_\Sigma),$$

and wherein diffusivity coefficient k represents uncertainty introduced by the noise in the velocity measurements.

In some embodiments, the standard deviation of TR is caused by noise in the velocity measurements, and wherein calculating the standard deviation of TR comprises utilizing the equation:

$$\sigma_{TR}(x, t) = \sqrt{S_R(x,t) - T_R^2(x,t)}$$

wherein SR and TR obey the equations:

$$\sigma_{TR}(x, t) = \sqrt{S_R(x, t) - T_R^2(x, t)}$$

$$\frac{\partial S_R}{\partial t} + \nabla \cdot (\vec{v} S_R) = 2T_R + \nabla \cdot (k\nabla S_R),$$

and wherein diffusivity coefficient k represents uncertainty introduced by the noise in the velocity measurements.

In some embodiments, a distribution of values of cumulative von-Mises stress at each instant of time and each point in space, which distribution of values of cumulative von-Mises stress is caused by noise in the velocity measurements, wherein a probability density function of distribution p(Σ, x, t) is calculated utilizing the equation:

$$\frac{\partial p}{\partial t} = -\frac{\partial (vp)}{\partial x} - \frac{\partial p}{\partial T} + \frac{\partial}{\partial x}\left(k\frac{\partial p}{\partial x}\right).$$

and wherein diffusivity coefficient k represents uncertainty introduced by the noise in the velocity measurements.

In some embodiments, a distribution of values of residence time emerges at each instant of time and each point in space, which distribution of values of residence time is caused by noise in the velocity measurements, wherein a probability density function of distribution p(T, x, t) is calculated utilizing the equation:

$$\frac{\partial p}{\partial t} = -\frac{\partial (vp)}{\partial x} - \frac{\partial (Sp)}{\partial S} + \frac{\partial}{\partial x}\left(k\frac{\partial p}{\partial x}\right).$$

and wherein diffusivity coefficient k represents uncertainty introduced by the noise in the velocity measurements.

In some embodiments, numerical metrics of blood flow are used to identify size, location, or both, of high blood plasma free hemoglobin (PfHb) within the cardiac chamber or blood vessel.

In some embodiments, a LVAD is surgically implanted into the subject. In some embodiments, LVAD is temporarily implanted into the subject. In some embodiments, the LVAD is a catheter-based LVAD.

In some embodiments, methods provided herein include evaluating an intraventricular region of hemolysis inside a cardiac chamber or blood vessel of a second subject comprising: implanting a LVAD into the second subject at a second location, wherein the LVAD operates under a second set of operating parameters; obtaining flow-velocity images of blood inside a cardiac chamber or blood vessel of the first subject; calculating hemolysis using the flow-velocity images using the following equation:

$$\frac{\Delta PfHb}{Hb} = C \sum\nolimits^a T_R^{b-1}$$

wherein PfHb is the plasma free hemoglobin, Hb is the total hemoglobin in the blood (intracellular and extracellular), Σ is the cumulative fluid shear stress experienced by blood particles in seconds−1, TR is the residence time of the blood particles in seconds, and a, b, and c are empirical constants; wherein Σ is determined using the forced transport equation:

$$\frac{D\sum}{Dt} = \partial_t \sum + \nabla \cdot \left(v \sum\right) = S,$$

$$\sum(x, t = 0) = 0,.$$

$$\sum(x_{inlet}, t) = 0,$$

wherein S is the Von-Mises stress at each point of space and time inside the left ventricle, and wherein S is determined from a velocity field obtained from the flow-velocity images. In some embodiments, the first location, the second location, or both is the location of cannula placement. In some embodiments, the first set of operating parameters, the second set of operating parameters, or both includes pump speed. In some embodiments, the cardiac chamber of the second subject is the left ventricular chamber.

In some embodiment of methods provided herein, the subject, the first subject, or the second subject is a mammal. In some embodiments, the mammal is a human. In some embodiments, the mammal is selected from the group consisting of: a monkey, a dog, a cat, a cow, a horse, a pig, a rat, and a mouse.

The section headings used herein are for organizational purposes only and are not to be construed as limiting the described subject matter in any way. When definitions of terms in incorporated references appear to differ from the definitions provided in the present teachings, the definition provided in the present teachings shall control. It will be appreciated that there is an implied "about" prior to metrics such as temperatures, concentrations, and times discussed in the present teachings, such that slight and insubstantial deviations are within the scope of the present teachings herein. In this application, the use of the singular includes the plural unless specifically stated otherwise. Also, the use of "comprise," "comprises," "comprising," "contain," "contains," "containing," "include," "includes," and "including" are not intended to be limiting. It is to be understood that both the foregoing general description and the following detailed description are exemplary and explanatory only and are not restrictive of the invention. The articles "a" and "an" are used herein to refer to one or to more than one (i.e., to at least one) of the grammatical object of the article. By way of example, "an element" means one element or more than one element.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
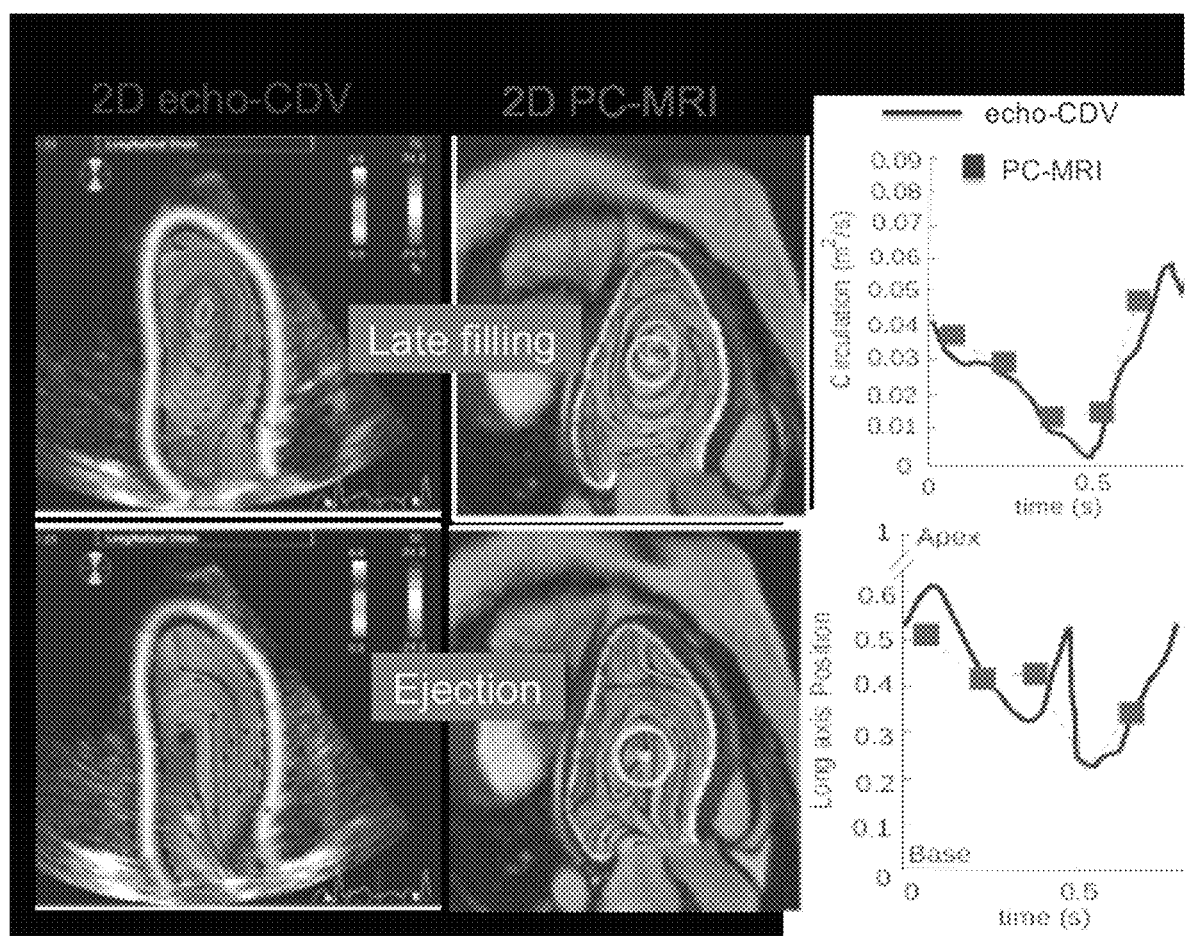
FIG. 1 displays head-to-head comparison of 2D echo-CDV and PCMRI by comparing flow maps and vortex stats. Panel A shows flow maps obtained by echo-CDV (left column) and phase-contrast MRI (right column) in a patient with dilated cardiomyopathy. The distributions of flow velocity and instantaneous streamlines are overlaid on anatomical images where, for echo-CDV, the LV wall is colored according to the values of longitudinal myocardial strain and the identified vortex structures are overlaid as yellow and cyan circles for the PCMRI and ultrasound methods, respectively. Panel B shows LV vortex circulation (top) and position (bottom) along the cardiac cycle, as measured by ultrasound (blue lines) and PCMRI (red squares) in the same patient.

A left ventricular assist device (LVAD) is a type of heart pump or mechanical circulatory support device implanted in selected patients. LVADs have been demonstrated to provide a safe and effective mechanical support in patients undergoing high-risk revascularization procedures and in patients with cardiogenic shock related to myocardial infarction. LVADs have also been demonstrated to be effective as bridge to transplantation or destination therapy in patients with end stage heart failure. Nonlimiting examples of left ventricular assist devices include Heartmate, Jarvik, Thoratec VAD, CentriMag, HeartWare, CorWave and Impella. Heartmate is an intermediate-to-chronic LVAD developed with the goal of providing up to 10 years of circulatory support for a broad range of advanced heart failure patients. Jarkvik augments the weakened heart's blood output to help restore a normal blood flow throughout the body and Thoratec is a device ideal for patients requiring extended left, right, or biventricular support. CentriMag, also known as Levitronix, is a temporary external VAD designed to be used as a short-term solution for acute heart failure while longer-term options are considered. HeartWare is a miniaturized pump capable of delivering up to 10 liters/minute of blood flow from the heart to the rest of the body and is being used in clinical trials for both bridge to transplantation and destination therapy. Impella is a minimally invasive cardiac assist device designed to partially unload the left ventricle thus reducing the heart's workload and oxygen consumption. CorWave is an LVAD that uses a pulsating membrane instead of a conventional pump.

In the LV of a diseased heart, progressive adverse remodeling leads to abnormal flow patterns that may impair pumping efficiency, and therefore affect the blood transit within the ventricle. Without wishing to be bound by theory, it is believed these abnormal intraventricular flow dynamics may contribute to the progression of certain diseases, leading to a final stage of heart failure (HF) (26, 27). Thus, it has been recognized that a deeper understanding of LV blood flow dynamics in normal and diseased LVs may enhance the current characterization of cardiac physiology and lead to a better knowledge of the pathophysiology of heart failure, facilitate subclinical diagnosis of cardiac diseases, improve tools used for characterizing, predict risk of thrombus formation and guide treatment strategies.

The present disclosure is based, in part, on the discovery of novel flow image-based method to identify advantageous or beneficial positioning and/or settings of LVADs that maximizes device stability, performance, and intraventricular blood transport, while minimizing hemolysis and intraventricular stasis risk. In some embodiments, provided herein are methods to assess the location and extent of intraventricular stasis regions inside a cardiac chamber or blood vessel (e.g., intraventricular stasis regions in a subject having a LVAD) by digital processing flow-velocity images obtained either by phase-contrast magnetic resonance (PCMR), 2D color-Doppler velocimetry (echo-CDV), echo-particle-image-velocimetry (echo-PIV), synthetic aperture ultrasound imaging, ultrasound vector velocimetry by transverse oscillation, direct PIV obtained by optical scanning of natural or artificial blood flow tracers. In general, any method suitable for providing a spatio-temporal distribution of flow velocity inside the cardiovascular system can be used. Approaches provided herein are based, at least in part, on quantifying the distribution of the blood Residence Time (TR) from time-resolved blood velocity fields in the cardiac chamber or blood vessel. In some aspects, methods provided herein enable in-vivo assessment of the location and extent of the stasis regions in the LV cardiac chamber or blood vessel (e.g., in a subject having a LVAD). Original metrics developed to integrate flow properties into simple scalars suitable for a robust and personalized assessment of the risk of thrombosis are provided herein. The early prediction of blood stasis in a cardiac chamber or blood vessel (e.g., in a subject having a LVAD) allows for directed use of anticoagulant or other (e.g., mechanical, surgical, or electrophysiological) therapy for the purpose of primary and secondary prevention, which, ultimately, result in a decreased occurrence of strokes.

The early prediction of blood stasis in a cardiac chamber or blood vessel (e.g., in a subject having a LVAD) may result in a decrease in strokes by appropriate use of anticoagulant therapy, appropriate use of mechanical surgical or procedural treatments to remove or alter cardiac structures or exclude blood flow from structures via intracardiac or extracardiac devices, or appropriate use of electrophysiologic surgical or procedural therapies to alter and/or ablate electrical heart rhythms and/or conduction patterns in the heart (including atrial fibrillation ablation) for the purpose of primary and secondary prevention. It may also have a significant impact on left ventricular assist device (LVAD) device design and operation set-up. For example, LVAD positioning, speed, and/or other operating variable may be adjusted based on the results obtained by using methods described herein, and the risk for hemolysis and/or thrombosis in subjects having a LVAD can be minimized.

In certain embodiments, methods disclosed herein include direct measurement of blood flow inside the cardiac chambers (e.g., in subject having a LVAD), instead of on numerical simulations of said flow, which are computationally expensive, and usually rely on geometrical oversimplifications about the heart's anatomy (e.g. valves, papillary muscles, trabeculae carnae, etc.), as well as oversimplified models of blood rheology. In some aspects, methods provided herein are based on the solution of a transport equation to obtain the spatiotemporal distribution of residence time inside the cardiac chambers, which is much more efficient than releasing virtual particles and tracking their trajectories. The approach can be used to analyze cardiac imaging data obtained using standard modalities. These innovations make the disclosed method more reliable and better suited for 1) high-throughput clinical use and seamless integration within existing medical imaging devices and software tools, 2) evaluation of blood stasis and hemolysis in the four cardiac chambers rather than just in the left ventricle.

In some aspects, methods disclosed herein (e.g., methods for identifying regions of blood flow stasis inside a cardiac chamber or blood vessel of a subject with a LVAD, methods for evaluating intraventricular flow shear stresses and their dependence on LVAD pump speed and cannula placement, or methods for calculating blood transport inside any cardiac chamber or blood vessel of a subject having a LVAD) include identifying regions of blood flow stasis inside a cardiac chamber or blood vessel of a subject having an implanted LVAD by obtaining flow-velocity images of blood inside a cardiac chamber or blood vessel of the subject, and calculating the residence time (TR), the standard deviation of the residence time (σR), kinetic energy, and/or rate of distortion of blood particles. As used herein, a "blood particle" is defined as a fluid parcel of blood containing a very small amount of fluid that is identifiable throughout its dynamic history while moving with the blood flow.

In some embodiments, generating numerical metrics of blood flow comprises calculating the blood flow's residence time (TR) inside the cardiac chamber or blood vessel (e.g., in subject having a LVAD). In some embodiments, generating numerical metrics of blood flow comprises calculating the standard deviation of the residence time (σR) inside the cardiac chamber or blood vessel. In some embodiments, generating numerical metrics of blood flow comprises calculating both the blood flow's residence time (TR) and the standard deviation of the residence time (σR) inside the cardiac chamber or blood vessel. In some embodiments, generating numerical metrics of blood flow comprises comparing the flow's residence time (TR) versus its standard deviation (σR) inside the cardiac chamber or blood vessel. In some embodiments, in regions of a cardiac chamber or blood vessel where TR is high compared to σR, the identification and/or estimation of blood stasis is statistically more significant than in regions where TR is low compared to σR. In some embodiments, regions of a cardiac chamber or blood vessel where TR−σR, or TR−[2σ] R and/or TR−[3σ] R, etc. are higher than a reference value (e.g., the value of TR observed in a cohort of patients that developed a thrombus in a clinical study) are identified as regions of blood flow stasis. In some embodiments, regions of blood flow stasis are identified with a statistical significance of about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or greater. In some embodiments, regions of blood flow stasis that are identified with statistical significance are predictive of risk of intracardiac or intravascular thrombus or of embolism (e.g., in a subject having a LVAD). In some embodiments, in regions of a cardiac chamber or blood vessel where the ratio of TR to σR is higher than a reference ratio of TR to σR (e.g., the ratio of TR to σR observed in a cardiac chamber or blood vessel of a healthy subject), the identification and/or estimation of blood stasis is statistically more certain than where the ratio of TR to σ(R) is about the same or lower than the reference ratio of TR to σR. In some embodiments, regions of a cardiac chamber or blood vessel where the ratio of TR to σR is high compared to a reference ratio (e.g., the ratio of TR to σR observed in a cardiac chamber or blood vessel of a healthy subject) are identified as regions of blood flow stasis, and are predictive of risk of intracardiac or intravascular thrombus or of embolism (e.g., in subject having a LVAD). In some embodiments, the observed ratio of TR to σR measured by using methods described herein is used (e.g., as a sole parameter or as one of several parameters) to guide LVAD positioning, speed, and/or other operating variable to reduce the risk for hemolysis and/or thrombosis in subjects having a LVAD.

In some embodiments, generating numerical metrics of blood flow (e.g., in subject having a LVAD) comprises calculating additional descriptors of the probability distribution of the values of the residence time (e.g., skewness, kurtosis, median, inter-quartile range and/or other interpercentile ranges) at each point in space and instant in time, in order to estimate the statistical significance of the calculated values of TR.

In some embodiments, generating numerical metrics of blood flow comprises calculating the blood flow's kinetic energy inside the cardiac chamber or blood vessel (e.g., in subject having a LVAD). Kinetic energy measures the overall rate of motion of the blood particles inside a blood region. In some embodiments, low values of kinetic energy in a residual blood region (e.g., a blood region with high residence time) indicate that such region is stagnant and, therefore, prone to thrombosis. In some embodiments, generating numerical metrics of blood flow comprises calculating the standard deviation of the blood flow's kinetic energy inside the cardiac chamber or blood vessel. In some embodiments, generating numerical metrics of blood flow comprises calculating both the blood flow's kinetic energy and the standard deviation of the blood flow's kinetic energy inside the cardiac chamber or blood vessel. In some embodiments, a kinetic energy that is low compared to the standard deviation of kinetic energy is indicative of blood flow stasis, and is predictive of risk of intracardiac or intravascular thrombus or of embolism (e.g., in subject having a LVAD). In some embodiments, observed kinetic energy measured by using methods described herein is used (e.g., as a sole parameter or as one of several parameters) to guide LVAD positioning, speed, and/or other operating variable to reduce the risk for hemolysis and/or thrombosis in subjects having a LVAD.

In some embodiments, generating numerical metrics of blood flow comprises calculating the blood flow's rate of distortion inside the cardiac chamber or blood vessel (e.g., in subject having a LVAD). The rate of distortion measures the rate at which the distances of adjacent blood particles change with time in the neighborhood of a given blood particle. In some embodiments, low values of rate of distortion in a residual blood region (e.g., a blood region with high residence time) indicate that such region is stagnant and, therefore, prone to thrombosis. In some embodiments, generating numerical metrics of blood flow comprises calculating the standard deviation of the blood flow's rate of distortion inside the cardiac chamber or blood vessel. In some embodiments, generating numerical metrics of blood flow comprises calculating both the blood flow's rate of distortion and the standard deviation of the blood flow's rate of distortion inside the cardiac chamber or blood vessel. In some embodiments, a rate of distortion that is low compared to the standard of deviation of the rate of distortion is indicative of blood flow stasis, and is predictive of risk of intracardiac or intravascular thrombus or of embolism (e.g., in subject having a LVAD). In some embodiments, an observed rate of distortion measured by using methods described herein is used (e.g., as a sole parameter or as one of several parameters) to guide LVAD positioning, speed, and/or other operating variable to reduce the risk for hemolysis and/or thrombosis in subjects having a LVAD.

In some embodiments, generating numerical metrics of blood flow comprises calculating a blood stasis timescale index (e.g., in subject having a LVAD). As used herein, a "blood stasis timescale index" is an index that is inversely related to the rate of distortion, and that measures the amount of it that takes the flow to deform a given blood particle by an amount comparable to the size of the blood particle. In some embodiments, high values of a blood stasis timescale index in a residual blood region (e.g., a blood region with high residence time) indicate that such region is stagnant and, therefore, prone to thrombosis.

In some aspects, methods disclosed herein utilize a spatiotemporal velocity map of blood flow in the heart as the input, together with anatomical images that are used to segment the walls of the cardiac chambers (e.g., in subject having a LVAD). This data may be obtained using color Doppler echocardiographic imaging, MRI with 4D flow, or other medical imaging techniques that provide velocity maps. The input data can consist of 2D or 3D time-resolved image data. The velocity data can be used to solve a transport equation with unit forcing using the segmented wall positions to impose no penetration boundary conditions. This solver provides the spatiotemporal distribution of the blood residence time inside the cardiac chambers (TR). The residence time distribution can be analyzed using spatiotemporal clustering algorithms to identify residual regions with relative decreased mixing from incoming flow.

In some aspects, methods disclosed herein (e.g., methods for identifying regions of blood flow stasis inside a cardiac chamber or blood vessel of a subject, methods for estimating risk of intracardiac or intravascular thrombus or of embolism originating in a cardiac chamber or blood vessel in a subject, or methods for calculating blood transport inside any cardiac chamber or blood vessel of a subject having a LVAD) include generating a residence time (TR) map, a kinetic energy map, and/or a rate of distortion map. In some embodiments, such maps are generated using numerical metrics of blood flow (e.g., numerical metrics of residence time (TR), kinetic energy, and/or rate of distortion of blood particles obtained from one or more flow-velocity images) to identify and characterize regions of blood flow stasis. In some embodiments, such maps are used to guide LVAD positioning, speed, and/or other operating variable to reduce the risk for hemolysis and/or thrombosis in subjects having a LVAD.

In some embodiments, methods disclosed herein include generating a map of the standard deviation of the residence time ($\sigma R$), a map of the standard deviation of kinetic energy, and/or a map of the standard deviation of the rate of distortion (e.g., in subject having a LVAD). In some embodiments, such maps are generated using numerical metrics of blood flow (e.g., numerical metrics of the standard deviation of the residence time ($\sigma R$), the standard deviation of kinetic energy, and/or the standard deviation of the rate of distortion of blood particles obtained from one or more flow-velocity images) to identify and characterize regions of blood flow stasis, particularly their statistical significance. In some embodiments, such maps are used to guide LVAD positioning, speed, and/or other operating variable to reduce the risk for hemolysis and/or thrombosis in subjects having a LVAD.

In some embodiments, a medical image-based apparatus is operated to obtain multiple flow-velocity images performed with different velocity scales (e.g., the encoding velocity in phase contrast MM or the color scale in Doppler echocardiography). In some embodiments, one or more flow-velocity images are performed with velocity scales that are significantly lower than the scales that are typically used (e.g., about 20 percent, about 25 percent, about 30 percent, about 35 percent, about 40 percent, about 45 percent, about 50 percent, about 55 percent, about 60 percent, about 65 percent, about 70 percent, about 75 percent, about 80 percent, or more lower than the scales that are typically used), in addition to one or more flow-velocity images that are performed with the typically-used velocity scales. In some embodiments, the data from the obtained multiple flow-velocity images are retrospectively merged in order to expand the dynamical range of the velocity measurements. In some embodiments, data from the obtained flow-velocity images are retrospectively merged to generate residence time (TR), kinetic energy, and/or rate of distortion maps. In some embodiments, data from the obtained flow-velocity images are retrospectively merged to generate maps of standard deviation of residence time ($\sigma R$), standard deviation of kinetic energy, and/or standard deviation of rate of distortion. Obtaining multiple flow-velocity images as described herein is useful in preventing overestimation of the residence time when there are regions where the blood velocity falls below the minimum measurable velocity of a single velocity scale acquisition (e.g., a velocity scale acquisition that is typically used). In some embodiments, the medical image-based apparatus is operated to obtain 2, 3, 4, 5, 6, 7, 8, 9, 10 or more flow-velocity images (e.g., one, two, or three-dimensional flow-velocity images resolved in time) performed with different velocity scales. In some embodiments, these residence time and flow velocity maps are then further processed to provide numerical metrics of blood stasis and the locations of regions with increased stasis. For example, the blood flow's kinetic energy, defined as $K=\frac{1}{2}(u^2+v^2+w^2)$, where u, v and w are the three components of the flow velocity in an orthogonal coordinate system, can be determined. However, kinetic energy is not a Galilean invariant and it could be possible for a fluid parcel to have high values of K while moving with little distortion, similar to a rigid solid. Thus, the distortion of fluid particles, which is quantified by the second invariant of the symmetric strain tensor, $Q_{ij}=(du_j/dx_j+du_j/dx_i)/2$, can also be computed. For an incompressible flow, the first invariant of $S_{ij}$ is zero and the second invariant is defined as $Q_S$=trace $(S_{ij}2)/2$. Note that $Q_S$ has dimensions of squared inverse of time, so it can be used to define a second stasis timescale $T_S=Q_S^{-1/2}$ in addition to TR.

In some embodiments, the size, position, shape, mobility, distance to cardiac wall, average kinetic energy and average distortion time of each spatio-temporally clustered residual volume are measured as a function of time (e.g., in subject having a LVAD). In some embodiments, colocalization and relative values of different metrics are also analyzed. Together with the number of residual volumes, this analysis provides a set of parameters that can be used to build a patient-specific risk index of blood stasis and risk of thrombus formation in the cardiac chambers (e.g., in subject having a LVAD) based on non-invasive clinical images. In some embodiments, this analysis provides a set of parameters that can be used to guide LVAD positioning, speed, and/or other operating variable to reduce the risk for hemolysis and/or thrombosis in subjects having a LVAD.

In some embodiments, provided herein are methods useful for the characterization (e.g., clinical evaluation, diagnosis, classification, prediction, profiling) of a subject's risk of intracardiac thrombus formation and for predicting whether and to what extent the subject may benefit from treatment. In some embodiments, provided herein are methods useful for the characterization (e.g., clinical evaluation, diagnosis, classification, prediction, profiling) of a subject's risk of intracardiac thrombus formation after having been implanted with a LVAD. As used herein, diagnosing includes both diagnosing and aiding in diagnosing. Other diagnostic criteria may be evaluated in conjunction with the results of methods provided herein in order to make a diagnosis. In some embodiments, a diagnosis can be used to guide LVAD positioning, speed, and/or other operating variable to reduce the risk for hemolysis and/or thrombosis in subjects having a LVAD.

The term "subject" refers to an animal or human. Preferably, the subject is a human. Subjects can also include non-human mammals. A human subject can be known as a patient. In some embodiments, the patient is experiencing or known to have experienced in sinus rhythm with LV systolic dysfunction. Such patients are known to be at increased risk of thrombus formation and subsequent embolic events (e.g. stroke) but currently the vast majority of them are not being identified and treated with any anticoagulation therapy, resulting in a high degree of morbidity and mortality. In some embodiments, the patient has been implanted with a LVAD.

In some embodiments, the patient is experiencing or known to have experienced atrial fibrillation. Currently, such patients are risk-stratified based only on the basis of demographic and comorbidity data based on previous cohorts, but no patient-specific tools exist to optimally determine for which patients the risk/benefit of anticoagulation is favorable.

In some embodiments, the patient has an implanted left ventricular assist device (LVAD) and is at increased risk of thrombus formation. Thrombi in these patients can cause systemic emboli as well as LVAD dysfunction. In some embodiments, methods provided herein are used to determine: 1) pre-surgical optimization of device selection, 2) optimization of device implantation, 3) optimization of LVAD settings including, but not limited to, pump speed alteration, pump speed modulation, and the use of pump settings to generate intermittent pulsatile flow, and 4) identification of patients for whom the risk/benefit of anticoagulation therapy is favorable.

In some embodiments, provided herein are methods for the communication of results or diagnoses or both to technicians, physicians or patients. In certain embodiments, computers are used to communicate assay results or diagnoses or both to interested parties, e.g., physicians and their patients. In some embodiments, a diagnosis or result (e.g., result indicating the effectiveness or risk of LVAD positioning or settings) is communicated to the subject as soon as possible after the diagnosis is obtained. The diagnosis or result may be communicated to the subject by the subject's treating physician. Additionally or alternatively, the diagnosis or result may be sent to a test subject by email or communicated to the subject by phone. The diagnosis may be sent to a test subject by in the form of a report. A computer may be used to communicate the diagnosis or result by email or phone. In certain embodiments, the message containing diagnosis or result may be generated and delivered automatically to the subject using a combination of computer hardware and software which will be familiar to artisans skilled in telecommunications.

The terms "decrease", "decreased", "reduced", "reduction" or 'down-regulated" are all used herein generally to mean a decrease by a statistically significant amount. However, for avoidance of doubt, "reduced", "reduction", "decreased" or "decrease" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold decrease, or any decrease between 1.0-fold and 10-fold or greater as compared to a reference level.

The terms "increased", "increase" or "up-regulated" are all used herein to generally mean an increase by a statistically significant amount; for the avoidance of any doubt, the terms "increased" or "increase" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold increase, or any increase between 1.0-fold and 10-fold or greater as compared to a reference level.

REFERENCES

1. Goldberg R J, Spencer F A, Gore J M, Lessard D, Yarzebski J. Thirty-year trends (1975 to 2005) in the magnitude of, management of, and hospital death rates associated with cardiogenic shock in patients with acute myocardial infarction: a population-based perspective. Circulation 2009; 119:1211-9.
2. Ponikowski P, Voors A A, Anker S D et al. 2016 ESC Guidelines for the diagnosis and treatment of acute and chronic heart failure: The Task Force for the diagnosis and treatment of acute and chronic heart failure of the European Society of Cardiology (ESC) Developed with the special contribution of the Heart Failure Association (HFA) of the ESC. Eur Heart J 2016; 37:2129-200.
3. Thiele H, Zeymer U, Neumann F J et al. Intraaortic balloon support for myocardial infarction with cardiogenic shock. N Engl J Med 2012; 367:1287-96.
4. O'Neill W W, Schreiber T, Wohns D H et al. The current use of Impella 2.5 in acute myocardial infarction complicated by cardiogenic shock: results from the USpella Registry. J Interv Cardiol 2014; 27:1-11.
5. Ouweneel D M, Eriksen E, Sjauw K D et al. Percutaneous Mechanical Circulatory Support Versus Intra-Aortic Balloon Pump in Cardiogenic Shock After Acute Myocardial Infarction. Journal of the American College of Cardiology 2017; 69:278-287.
6. Pedrizzetti G and Domenichini F. Left Ventricular Fluid Mechanics: The Long Way from Theoretical Models to Clinical Applications. *Annals of biomedical engineering*. 2014.
7. Bermejo J, Martinez-Legazpi P and Alamo J Cd. The Clinical Assessment of Intracardiac Flows. *Ann Rev Fluid Mech*. 2015; 47.
8. Wigstrom L, Ebbers T, Fyrenius A, Karlsson M, Engvall J, Wranne B and Bolger A F. Particle trace visualization of intracardiac flow using time-resolved 3D phase contrast MRI. *Magn Reson Med*. 1999; 41:793-799.
9. Kilner P J, Yang G Z, Wilkes A J, Mohiaddin R H, Firmin D N and Yacoub M H. Asymmetric redirection of flow through the heart. *Nature*. 2000; 404:759-761.
10. Zhang Z, Friedman D, Dione D P, Lin B A, Duncan J S, Sinusas A J and Sampath S. Assessment of left ventricular 2D flow pathlines during early diastole using spatial modulation of magnetization with polarity alternating velocity encoding: A study in normal volunteers and canine animals with myocardial infarction. *Magnetic Resonance in Medicine*. 2013; 70:766-775.
11. Bolger A F, Heiberg E, Karlsson M, Wigstrom L, Engvall J, Sigfridsson A, Ebbers T, Kvitting J P, Carlhall C J and Wranne B. Transit of blood flow through the human left ventricle mapped by cardiovascular magnetic resonance. *J Cardiovasc Magn Reson*. 2007; 9:741-747.
12. Bermejo J, Benito Y, Alhama M, Yotti R, Martinez-Legazpi P, Perez del Villar C, Perez-David E, Gonzalez-Mansilla A, Santa-Marta C, Barrio A, Fernandez-Aviles F and del Alamo J C. Intraventricular vortex properties in nonischemic dilated cardiomyopathy. *American journal of physiology Heart and circulatory physiology*. 2014; 306:H718-29.
13. Hong G R, Pedrizzetti G, Tonti G, Li P, Wei Z, Kim J K, Baweja A, Liu S, Chung N, Houle H, Narula J and Vannan M A. Characterization and quantification of vortex flow in the human left ventricle by contrast echocardiography using vector particle image velocimetry. *JACC Cardiovascular imaging*. 2008; 1:705-17.
14. Eriksson J, Bolger A F, Ebbers T and Carlhall C J. Four-dimensional blood flow-specific markers of LV dysfunction in dilated cardiomyopathy. *European heart journal cardiovascular Imaging*. 2013; 14:417-24.
15. Abe H, Caracciolo G, Kheradvar A, Pedrizzetti G, Khandheria B K, Narula J and Sengupta P P. Contrast echocardiography for assessing left ventricular vortex strength in heart failure: a prospective cohort study. *European Heart Journal—Cardiovascular Imaging*. 2013; 14:1049-1060.
16. Hendabadi S, Bermejo J, Benito Y, Yotti R, Fernandez-Aviles F, Del Alamo J C and Shadden S C. Topology of blood transport in the human left ventricle by novel processing of Doppler echocardiography. *Annals of biomedical engineering*. 2013; 41:2603-16.
17. Wong K, Samaroo G, Ling I, Dembitsky W, Adamson R, Del Alamo J and May-Newman K. Intraventricular flow patterns and stasis in the LVAD-assisted heart. *Journal of biomechanics*. 2014; 47:1485-1494.
18. Rossini L, Martinez-Legazpi P, Vu V, Fernandez-Friera L, Perez del Villar C, Rodriguez-Lopez S, Benito Y, Borja M-G, Pastor-Escuredo D, Yotti R, Ledesma-Carbayo M J, Kahn A M, Ibanez B, Fernandez-Aviles F, May-Newman K, Bermejo J and del Alamo J C. A Clinical Method for Mapping and Quantifying Blood Stasis in the Left Ventricle. *Journal of biomechanics*. 2016; 49:2152-61.
19. Rossini L, Martinez-Legazpi P, Benito Y, Perez del Villar C, Gonzalez-Mansilla A, Borja M-G, Yotti R, Kahn A M, Fernandez-Aviles F, Bermejo J and del Alamo J C. Assessment of intraventricular blood transport in patients undergoing cardiac resynchronization therapy. *Meccanica*. 2016; Special Issue. Advances In Biomechanics: From Foundations To Applications.:1-14.
20. Rossini L, Martinez-Legazpi P, Vu V et al. A clinical method for mapping and quantifying blood stasis in the left ventricle. J Biomech 2016; 49:2152-61.
21. Garcia D, Del Alamo J C, Tanne D, Yotti R, Cortina C, Bertrand E, Antoranz J C, Perez-David E, Rieu R, Fernandez-Aviles F and Bermejo J. Two-dimensional intraventricular flow mapping by digital processing conventional color-Doppler echocardiography images. *IEEE transactions on medical imaging*. 2010; 29:1701-13.
22. Chakraborty P, Balachandar S and Adrian R J. On the relationships between local vortex identification schemes. *Journal of Fluid Mechanics*. 2005; 535:189-214.
23. Flores O, Jimenez J and Del Alamo J C. Vorticity organization in the outer layer of turbulent channels with disturbed walls. *Journal of Fluid Mechanics*. 2007; 591:145-154.
24. del Alamo J C, Jimenez J, Zandonade P and Moser R D. Self-similar vortex clusters in the turbulent logarithmic region. *Journal of Fluid Mechanics*. 2006; 561: 329-358.
25. Perry A E and Chong M S. A Description of Eddying Motions and Flow Patterns Using Critical-Point Concepts. *Annual Review of Fluid Mechanics*. 1987; 19:125-155.
26. Domenichini F, Pedrizzetti G. Intraventricular vortex flow changes in the infarcted left ventricle: numerical results in an idealised 3D shape. Comput Methods Biomech Biomed Engin 2011; 14:95-101.
27. Pedrizzetti G, La Canna G, Alfieri O, Tonti G. The vortex-an early predictor of cardiovascular outcome? Nat Rev Cardiol 2014; 11:545-53.
28. Yotti R, Bermejo J, Desco M M et al. Doppler-derived ejection intraventricular pressure gradients provide a 29. Perez Del Villar C, Bermejo J, Rodriguez-Perez D et al. The role of elastic restoring forces in right ventricular filling. Cardiovasc Res 2015; 107:45-55.
30. Cortina C, Bermejo J, Yotti R et al. Noninvasive assessment of the right ventricular filling pressure gradient. Circulation 2007; 116:1015-23.
31. Bermejo J, Yotti R, Perez del Villar C et al. Diastolic chamber properties of the left ventricle assessed by global fitting of pressure-volume data: improving the gold standard of diastolic function. J Appl Physiol 2013; 115:556-68.
32. Smiseth O A, Mjos O D. A reproducible and stable model of acute ischaemic left ventricular failure in dogs. Clin Physiol 1982; 2:225-39.
33. Yotti R, Bermejo J, Benito Y et al. Noninvasive estimation of the rate of relaxation by the analysis of intraventricular pressure gradients. Circ Cardiovasc Imaging 2011; 4:94-104.
34. Chan C H, Hilton A, Foster G, Hawkins K. Reevaluation of the Harboe assay as a standardized method of assessment for the hemolytic performance of ventricular assist devices. Artif Organs 2012; 36:724-30.
35. Paul R, Apel J, Klaus S, Schugner F, Schwindke P, Reul H. Shear stress related blood damage in laminar couette flow. Artif Organs 2003; 27:517-29.
36. Bermejo J, Benito Y, Alhama M et al. Intraventricular vortex properties in nonischemic dilated cardiomyopathy. Am J Physiol Heart Circ Physiol 2014; 306:H718-29.
37. Bermejo J, Martínez-Legazpi P, Álamo J Cd. The Clinical Assessment of Intraventricular Flows. Annual Review of Fluid Mechanics 2015; 47:315-342.
38. Hendabadi S, Bermejo J, Benito Y et al. Topology of blood transport in the human left ventricle by novel processing of Doppler echocardiography. Ann Biomed Eng 2013; 41:2603-16.
39. Garcia D, Del Alamo J C, Tanne D et al. Two-dimensional intraventricular flow mapping by digital processing conventional color-Doppler echocardiography images. IEEE Trans Med Imaging 2010; 29:1701-13.
40. Martinez-Legazpi P, Bermejo J, Benito Y et al. Contribution of the diastolic vortex ring to left ventricular filling. J Am Coll Cardiol 2014; 64:1711-21.
41. Rossini L, Martinez-Legazpi P, Benito Y et al. Clinical assessment of intraventricular blood transport in patients undergoing cardiac resynchronization therapy. Meccanica 2016; 52:563-576.
42. Seo J H, Abd T, George R T, Mittal R. A coupled chemo-fluidic computational model for thrombogenesis in infarcted left ventricles. Am J Physiol Heart Circ Physiol 2016; 310:H1567-82.
43. Bolger A F, Heiberg E, Karlsson M et al. Transit of blood flow through the human left ventricle mapped by cardiovascular magnetic resonance. J Cardiovasc Magn Reson 2007; 9:741-747.
44. Eriksson J, Bolger A F, Ebbers T, Carlhall C J. Four-dimensional blood flow-specific markers of LV dysfunction in dilated cardiomyopathy. Eur Heart J Cardiovasc Imaging 2013; 14:417-24.
45. Eriksson J, Carlhall C J, Dyverfeldt P, Engvall J, Bolger A F, Ebbers T. Semi-automatic quantification of 4D left ventricular blood flow. J Cardiovasc Magn Reson 2010; 12:9.
46. Eriksson J, Dyverfeldt P, Engvall J, Bolger A F, Ebbers T, Carlhall C J. Quantification of presystolic blood flow organization and energetics in the human left ventricle. Am J Physiol Heart Circ Physiol 2011; 300:H2135-41.
47. Fredriksson A G, Zajac J, Eriksson J et al. 4-D blood flow in the human right ventricle. Am J Physiol Heart Circ Physiol 2011; 301:H2344-50.
48. Therrien J, Siu S C, Harris L et al. Impact of pulmonary valve replacement on arrhythmia propensity late after repair of tetralogy of Fallot. Circulation 2001; 103:2489-94.
49. Chaturvedi R R, Kilner P J, White P A, Bishop A, Szwarc R, Redington A N. Increased airway pressure and simulated branch pulmonary artery stenosis increase pulmonary regurgitation after repair of tetralogy of Fallot. Real-time analysis with a conductance catheter technique. Circulation 1997; 95:643-9.
50. Hellums J D. 1993 Whitaker lecture: Biorheology in thrombosis research. Ann Biomed Eng. 1994; 22:445-455.
51. Ramstack J M, Zuckerman L, Mockros L F. Shear-induced activation of platelets. J Biomech. 1979; 12:113-125.
52. Vu V, Rossini L, Montes R, Campos J, Moon J, Martinez-Legazpi P, Bermejo J, del Alamo J C, May-Newman K. Mitral Valve Prosthesis Design Affects Hemodynamic Stasis and Shear In The Dilated Left Ventricle. Ann Biomed Eng. 2019. doi: 10.1007/s10439-019-02218-z.
53. Fraser K H, Zhang T, Taskin M E, Griffith B P, Wu Z J. A Quantitative Comparison of Mechanical Blood Damage Parameters in Rotary Ventricular Assist Devices: Shear Stress, Exposure Time and Hemolysis Index. J Biomech Eng. 2012; 134: 081002.

EXAMPLES

The invention is further described in the following examples, which do not limit the scope of the invention described in the claims.

Example 1

The present study is designed to implement a novel method for evaluating intraventricular flow shear stress and for measuring and mapping blood stasis in the heart. The purpose is to obtain individual quantitative metrics of global and regional stasis from flow-velocity measurements in the LV. The feasibility of the method is first tested by comparing high-resolution datasets of LV flow velocity by both 2D echo-CDV and phase-contrast magnetic resonance (PCMRI). To generalize the applicability of the tool, the method is also adapted to work with ultrasound data. Data from LVs before and after LVAD implantation is analyzed. The unique ability of the tool to identify and quantify cumulative blood shear stress, assess the risk of hemolysis, track regions at risk of blood stagnation, and provide qualitative and topological assessments of blood stasis in the LV is demonstrated.

Methods

Study Population 100 patients implanted with HeartWare HVAD devices prospectively participate in this study and provide echocardiography studies for 2D color Doppler velocimetry (echo- CDV) evaluation. For each patient, studies collected at the following timepoints are analyzed:

Baseline (prior to implant)
Implant—while in operating room.
Two Abbreviated Transesophageal Echos:
1) after implantation/once patient is off cardio-pulmonary bypass while chest is still open,
2) after chest closure.
Discharge (with Lavare on and off).
3 months post-implant.
6 months post-implant, including a ramp study with abbreviated echos for flow velocimetry acquired every 200 rpms.
12 months post-implant.

All the echocardiographic studies from each patient is analyzed to determine 2D velocity maps and derive a comprehensive database of flow parameters (vortex position, size and strength, blood shear mapping, residence time, pressure gradients, etc).

In order to evaluate the dependence on cannula positioning of hemolysis, blood stasis and other flow parameters that may correlate with outcomes, cannula positioning is imaged and parameterized with respect to LV anatomical features and also with respect to intraventricular flow features (e.g. the inflow jet).

Data from clinically indicated blood tests are collected from electronic medical records, including (if/when available) measures of hemolysis (Hb, LDH, plasma free-Hb), and basic lab samples including Hb, whitecount, platelets, Na, K, creatinine, BUN, liver function tests (LFTs). Data on complications (bleeding, thrombotic complications, worsening heart failure) are collected from the electronic medical records. Also, information regarding clinical outcomes (survival, need for additional mechanical support, need for heart transplantation, duration of hospital stays) is collected.

These data are analyzed to glean multivariate correlation and causality relationships between themselves and with cannula positioning, LVAD speed and flow parameters.

2D Echo Color Doppler Velocimetry.

The 2D echo-CDV algorithm analyzes standard color-Doppler sequences and provides time-resolved vector flow maps in the apical long axis view of the LV (defined by the apex and the center of the mitral and of the aortic valves) (7, 21). Patients routinely undergo echocardiograms as part of their standard care.

Echo-CDV only requires a few additional images, extending the duration of the study by ~5 minutes (21). Echo-CDV with phase-contrast was recently validated MRI in patients, obtaining good agreement between the two modalities (12) (FIG. 1).

Characterization of LV Vortex Patterns.

The flow vorticity, $\omega$, is used to characterize the flow structures and is computed as the curl of the velocity, $\omega = \nabla \times v$. LV vortices are identified in each instantaneous flow field using the second invariant of the velocity gradient tensor (22, 23). These flow patterns are tracked in time using a clustering algorithm for the analysis of vortices in turbulent flows (12, 24). They can be characterized by their circulation, kinetic energy, radius, aspect ratio, and the trajectory of their center. Circulation is defined as $\Gamma = \oint_\Omega \omega = (x, y) d\Omega$, where the 2D domain of integration, $\Omega$ is the inner core of the vortex. The position of the vortex center is $\{x_v, y_v\} = \oint_\Omega \{x, y\} \omega(x, y) d\Omega$. The radius of the vortex is defined by $$R = \sqrt{\frac{1}{\Gamma} \oint_\Omega [(x-x_v)^2 + (y-y_v)^2] \omega(x, y) d\Omega}$$

Cumulative Blood Shear Stress and Hemolysis

Figure 2:
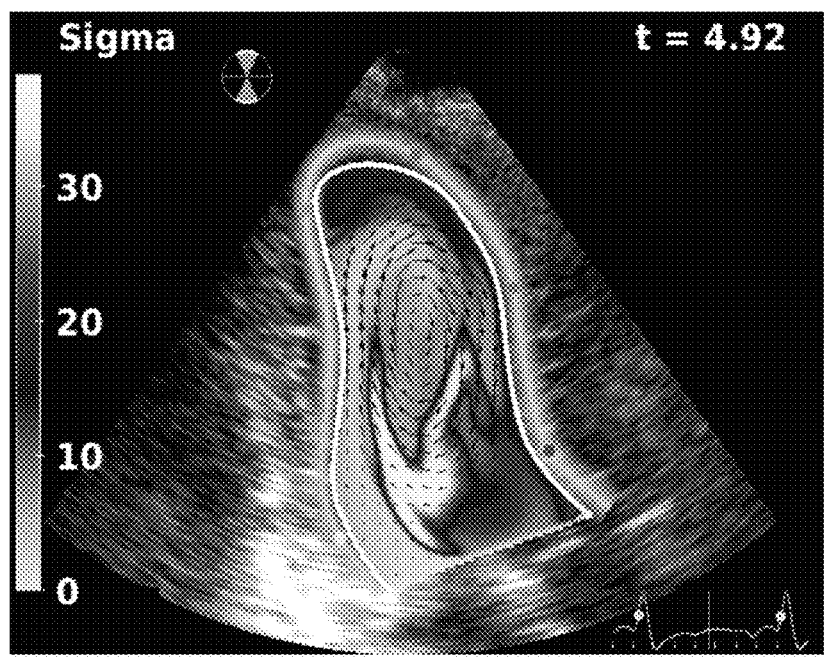
FIG. 2 displays a snapshot of cumulative blood shear at isovolumic contraction in a patient with LV dysfunction mapping, based on echo-CDV.

Hemolysis risk is assessed by a power-law model that predicts normalized hemolysis as $$\frac{\Delta PfHb}{Hb} = C \sum^a T_R^{b-1},$$

where PfHb is the plasma free hemoglobin, Hb is the total hemoglobin in the blood (intracellular and extracellular), $\Sigma$ is the cumulative fluid shear stress experienced by blood particles in seconds$^{-1}$, $T_R$ is their residence time in seconds (a.k.a. exposure time), and a=2.4, b=0.8 and C=3.6×10 AK are empirical constants. In this project, $\Sigma$ is determined using a forced transport equation, $$\frac{D\sum}{Dt} = \partial_t \sum + \nabla \cdot \left(v \sum\right) = S, \tag{1}$$

$$\sum(x, t = 0) = 0,$$

$$\sum(x_{inlet}, t) = 0,$$

where S is the Von-Mises stress at each point of space and time inside the left ventricle, determined from the velocity field obtained by echo-CDV in each patient. FIG. 2 shows an example map of $\Sigma$ obtained from a patient with LV dysfunction. The region of highest cumulative shear corresponds with the boundary of the LV vortex. Residence time is computed in a similar manner as described below.

Analysis of Blood Transport Efficiency

Using the time-dependent 2D echo-CDV velocity field v(x, t) and the LV wall tracking data as input, an advection equation is solved for a passive scalar field $\psi$ with uniform initial conditions and step-wise Dirichlet inflow boundary conditions, $$\frac{D\psi}{Dt} = \partial_t \psi + \nabla \cdot (v\psi) = 0, \tag{2}$$

$$\psi(x, t = 0) = \psi_0 = const,$$

$$\psi(x_{inlet}, 0 < t < t_1) = \psi_1 = const,$$

$$\psi(x_{inlet}, t_1 \le t < t_2) = \psi_2 = const,$$

etc.

Figure 3:
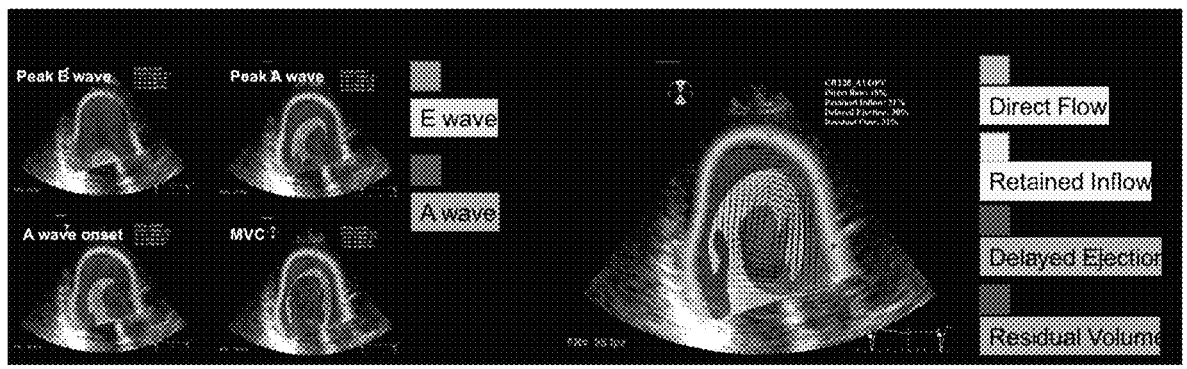
FIG. 3 displays examples of blood transport analysis based on echo-CDV. Panel A shows tracking of the volumes of blood that enter the LV during the E wave, shown in gold, and A wave, shown in red, in a human LV. Panel B shows segmentation of LV blood volumes in the same LV at aortic valve opening, showing direct flow (DF, green), retained inflow (RI, yellow), delayed ejection (DE, blue) and residual volume (RV, red).

This approach tags different volumes of blood with different numerical values that are transported by the flow, thereby simulating the visualization of distinct virtual contrast media inside the LV. For instance, one can implement a two-step inlet boundary condition to track the evolution of the two fluid volumes that enter the ventricle during the E wave and the A wave, and to determine the size of these structures and their frontal position (FIG. 3A).

In addition to tracking the filling transport patterns the spatiotemporal evolution of the blood that is ejected each cardiac cycle is analyzed by integrating equation (2) backwards in time. Combining the results from the backward and forward integrations allows one to automatically identify the following transport structures: direct flow (DF, blood that enters and exits the LV in the same cardiac cycle), retained inflow (RI, incoming blood that is not ejected during the same cycle), delayed ejection (DE, ejected blood that entered the LV in a previous cardiac cycle) and residual flow (RF, blood that entered the LV in a previous cycle and is not ejected in the current cycle, therefore residing in the LV for at least two cardiac cycles) (11) (FIG. 3B).

To systematically analyze the effect of LVAD support on LV filling transport, the fraction of LV size occupied by the E and A waves as well as the normalized apical position of each wave's front is determined. It is possible to combine this approach with our cumulative shear calculation method to assess the hemolysis risk of the blood pool that enters the LVAD device each cardiac cycle.

To assess the kinematic efficiency of flow redirection inside the LV under LVAD support, the size, kinetic energy density and acceleration of each transport region at the onset of systole is determined. Kinetic energy density is calculated from 2D echo-CDV data as $K(x, t) = |v|^2/2$. This variable is spatially integrated over the surface occupied by each transport region to obtain its overall value inside the region (e.g. $K_{DF} = \int_{S_{DF}} K(x)dx$). The ratio $\eta_K = K_{DF}/K_{LV}$ at aortic valve opening in all the patients is calculated to determine if LVAD support contributes to efficiently focusing the inflow kinetic energy into the volume of fluid that is ejected during systole. The ratio of direct flow area to total LV area in the imaging plane, $\eta_{DF} = S_{DF}/S_{LV}$, is also computed to quantify the efficiency of volumetric blood transport within one cardiac cycle. In addition, the efficiency of flow redirection is assessed by calculating the net acceleration transferred to the direct flow region in the direction of the LV outflow tract, normalized with the total magnitude of this acceleration, $$\eta_M = \frac{M_{DF} \cdot e_{LVOT}}{|M_{DF}|},$$

where $e_{LVOT}$ is the unitary vector parallel to the direction of the LV outflow tract, pointing outwards the LV. Fluid acceleration will be calculated as $$M(x, t_0) = \left(\frac{\partial v}{\partial t} + v \cdot \nabla v\right).$$

The orientation of the whole ventricle's M with respect to the LV long axis indicates the degree of alignment between the hemodynamic pressure forces and the inflow/outflow tract.

Blood Residence Time and Stasis.

The time spent by blood particles inside the LV (TR, residence time) is calculated using a forced transport equation, $$\frac{DT_R}{Dt} = \partial_t T_R + \nabla \cdot (v T_R) = 1, \quad (3)$$

$$T_R(x, t = 0) = 0,$$

$$T_R(x_{inlet}, t) = 0,$$

as explained previously (18).

The TR distributions of each patient is analyzed for each value of the LVAD speed setting. Residual blood volumes that do not mix with the fresh blood entering the LV each cardiac cycle are automatically segmented, which are potentially stagnant.

Spatio-temporally connected pixels with high residence time (higher than a given threshold $T_0$, e.g. TR>2 sec) are clustered using algorithms (12, 24), and stored for further analysis. For each segmented residual volume, the spatiotemporally averaged stasis indices such as kinetic energy are calculated. For each segmented residual volume, stasis indices such as the kinetic energy (K) or the distortion timescale $T_S = 1/\sqrt{Q_S}^{13}$ is calculated, where $Q_S$ is the 2nd invariant of the fluid's symmetric strain tensor S (25). Low K or/and high Ts are indicators of blood stasis.

Figure 4:
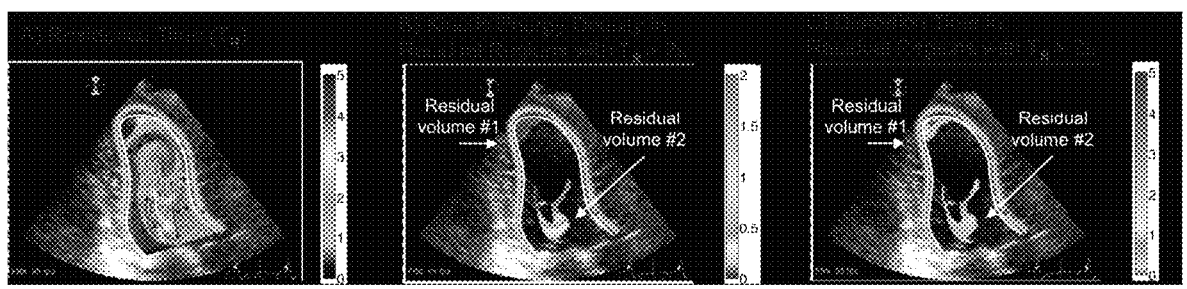
FIG. 4 displays a snapshot of blood stasis indices at isovolumic contraction in a patient with LV dysfunction. Panel A shows intraventricular residence time TR and instantaneous streamlines, Panel B shows Kinetic Energy Density (K) in the two residual volumes with TR>2 sec, and Panel C shows Distortion time (TS) in the same residual volumes.

This methodology is illustrated for the diseased LV shown in FIG. 4, where two residual blood volumes with TR>2 sec were identified. These data and recent work (18) suggest that the proposed analysis is able to identify blood volumes that are at high risk of stasis.

Mapping Hemodynamic Pressure Gradients.

Figure 5:
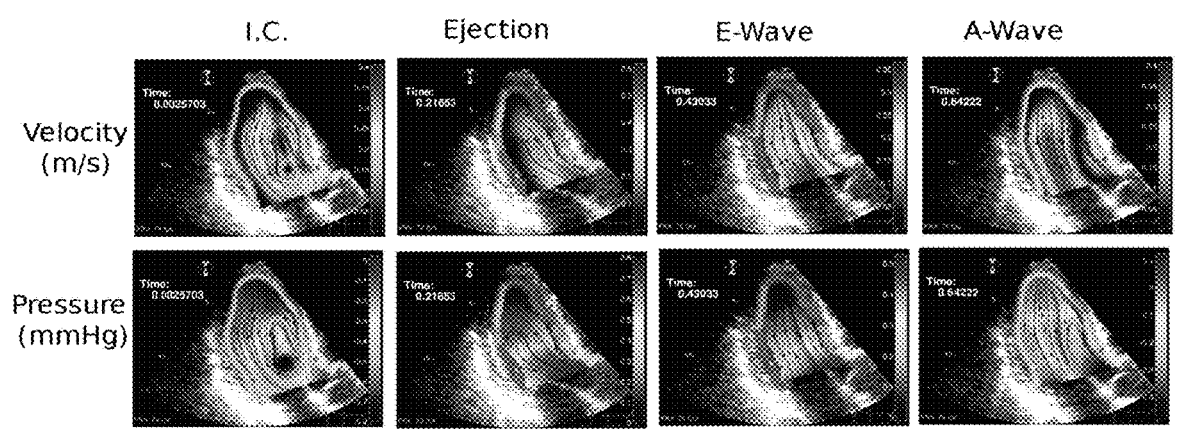
FIG. 5 displays Echo 2D velocity fields and hemodynamic pressure maps. Each panel represents a different instant of the cardiac cycle, where $1^{st}$ column shows isovolumetric contraction (I.C.), $2^{nd}$ column shows ejection, $3^{rd}$ column shows early filling and $4^{th}$ column shows late filling.

An algorithm to calculate pressure maps from echo 2D flow velocity data has been calculated. The algorithm is based on enforcing mass conservation and leads to the integration of a Poisson equation for the pressure p, with boundary conditions on the moving walls of the LV.

$$\nabla^2 p = -\nabla \cdot (v \cdot \nabla v), \text{ inside the } LV \quad (4)$$

$$\nabla p \cdot n = -\left[\frac{\partial v}{\partial t} + v \cdot \nabla v\right] \cdot n, \text{ at the } LV \text{ walls},$$

where n is the vector perpendicular to the LV walls at each position of the wall. This equation is integrated using a numerically efficient multigrid method and the boundary conditions are imposed using a sharp interface immersed boundary method. FIG. 5 shows an example of the pressure maps obtained by our algorithm from echocardiographic imaging.

Cannula Positioning.

Cannula positioning is imaged by echocardiography in the parasternal (or mid-esophageal for intraoperative imaging) long axis view. Its position is parameterized by the distance between the aortic valve and the tip of the cannula is measured and normalized with the long axis length of the ventricle. The normalized distance of the cannula to the inferolateral and anteroseptal walls of the LV is measured and used to parameterize cannula positioning. In addition to the orientation of the cannula with respect to anatomical structures, it is postulated that its orientation with respect to flow structures may be a relevant parameter that dictates shear stresses, residence time, etc. Thus, the distance and relative orientation between the cannula and the axis of the flow filling jet of the LV is also determined.

Summary

The main objective of this exploratory study is non-invasive quantification of intraventricular flow using echo to better understand how the speed of the HeartWare HVAD device and its placement affect the risk of thrombus formation, hemolysis, and patient outcomes. A secondary objective of this work is to assess whether non-invasive blood flow imaging could be incorporated as a tool to guide device implantation and clinically manage HVAD implanted patients. To achieve this objective, echocardiographic studies on a subgroup of ~100 patients implanted with the HVAD enrolled in The HeartWare MCS Destination Therapy Post-Approval Study were analyzed. Novel software to quantify the blood flow velocity fields in the LV of these patients is used. These data are used to characterize the dynamics of LV blood flow patterns (e.g. diastolic vortices), the efficiency of blood transport, the LV residence time of blood and the cumulative shear stress experienced by blood cells. These parameters are correlated to clinical data including blood labwork and outcome data (hemolysis, thrombosis).

Example 2

The present study is designed to determine the effects of position and speed setting of the Impella system on 1) intraventricular flow patterns, 2) hemolysis, 3) intraventricular blood stasis, and 4) its impact on blood transport and left ventricular filling. To achieve this objective, an experimental study is performed in a porcine model (n=10) using a controlled factorial design. Flow and device parameters are correlated to the risk of hemolysis by analyzing blood samples in each of the stages of study. Non-invasive quantification of intraventricular flow using novel imaging techniques such as echo-CDV may be useful to identify the best settings and locations of the Impella system.

Methods

A total of ten (10) adult minipigs (~60 kg) undergo instrumentation and flow-imaging experiments. Anesthesia is induced with intravenous propofol (1.5 mg/kg) and fentanyl (5 µg/kg) and the animals are endotracheally intubated and mechanically ventilated without end-expiratory positive pressure. Complete anesthesia is maintained by propofol (0.2 mg/kg/min) and fentanyl (5-10 mg/kg/h) endovenous infusion. The abolition of eye reflexes, blood pressure, and heart rate are systematically monitored to ensure deep anesthesia and good oxygenation and ventilation is ensured by arterial blood gas analysis (28, 29).

Femoral and internal carotid vascular packages are dissected and the cannulation of central arterial and venous access is performed by Seldinger's technique. A right jugular approach is used to place a Swan-Ganz catheter in the pulmonary artery to measure cardiac output. Invasive arterial blood pressure monitoring and arterial blood sample collection are performed through left carotid artery cannulation. After completing vascular accesses, anticoagulation is initiated and maintained with repeated bolus of sodium heparine (100 UI/kg/2 h). A subxifoid subcutaneous incision is made in order to optimize apical echocardiographic images (28-31).

Figure 7:
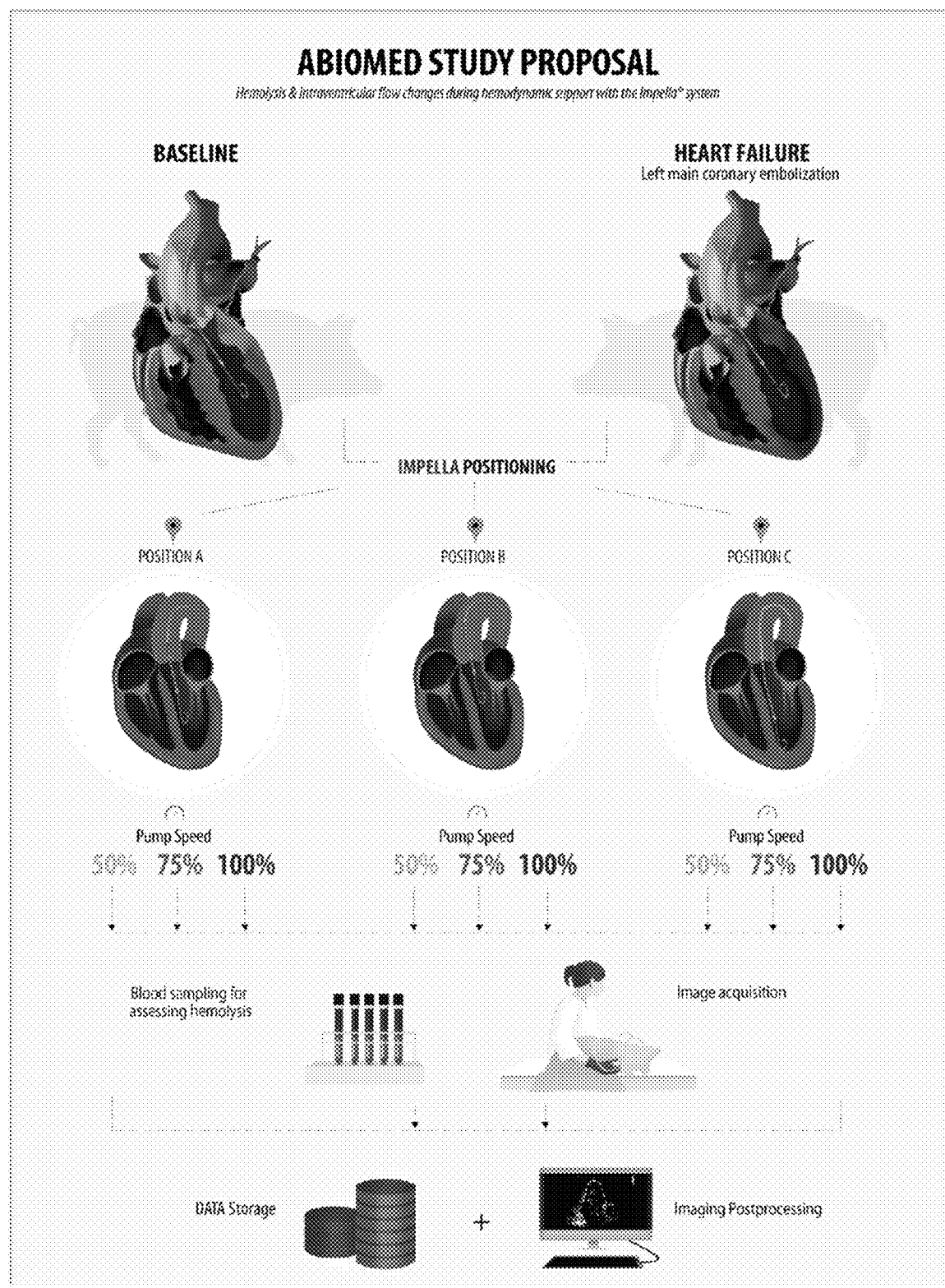
FIG. 7 displays an exemplary study design where a factorial 3 (positions)×3 (speeds)×3 (degrees of LV dysfunction) experiment is performed in a porcine model (n=10) of acute heart failure induced by coronary microsphere embolization. This design allows for creation of a large matrix of the studied parameters (LV function, position and speed combinations) and the measured flow and hemolysis metrics.

Through the right femoral artery an Impella® catheter pump is placed in the LV and connected to an external console which consists of an integrated controller for the pump and purge system (Automated Impella® Controller, Abiomed). Impella's placement is guided using transthoracic (TTE) echocardiography in the parasternal long-axis and apical views. A modified inlet of the Impella® catheter is preferred with a plastic head to avoid undesirable ultrasound reverberations and drop-outs when acquiring images. Each animal is studied at baseline and after inducing severe acute left ventricular dysfunction by left main coronary microspheres embolization (HF, see FIG. 7) (n=4) as previously reported in other experiments or our group (28, 32, 33).

A standard 6.5F JL3 coronary artery catheter is advanced via a femoral artery into the left main coronary artery during fluoroscopy. Polystyrene microspheres (45 µm, Polysciences) are diluted with dextran and saline to a solution of 1 mg microspheres per ml. The microsphere solution is injected through the coronary catheter as 5 ml boluses about 5 min apart. The embolization is complete when the LV ejection fraction measured by 2D echocardiography (Simpson biplane) decrease below 35%. Serial measurements varying the Impella® location and its speed are obtained in baseline, at moderate degrees of LV dysfunction (LV EF 40%) and after 20 min of completing embolization phases (see FIG. 7). Animals are euthanized at the end of the experiments with intravenous sodium-pentobarbital (100 mg/kg). The local Institute Animal Care Committee must approve the experimental protocol. All animal procedures must be in accordance with guidelines from Directive 2010/63/EU.

Impella® Adjustment of Positioning and Speed

Figure 8:
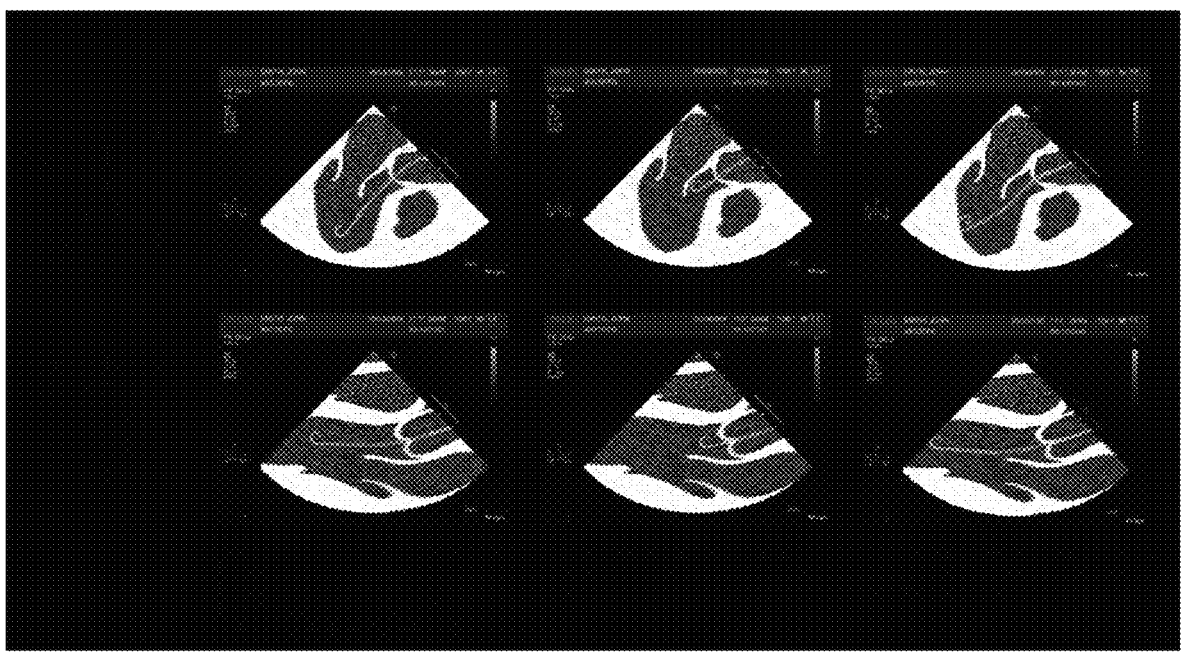
FIG. 8 displays different LVAD positions. $1^{st}$ row shows TEE mid-esophageal 135 degrees view sketch and $2^{nd}$ row shows TTE parasternal long-axis view sketch. $1^{st}$ column shows Position A, $2^{nd}$ column shows Position B and $3^{rd}$ column shows Position C.

During each of these 3 phases, the location of the catheter is modified and placed in the following positions:

1) Position A: The Impella® catheter is set at high thrust condition, lying along the inner curve of the aorta and placing the positioning marker approximately at the aortic valve. The aim is to settle the pump inlet approximately 4 cm distal to the aortic valve. The goal is to ensure avoiding the subannular position or any position that interferes with the anterior mitral leaflet or entrain the catheter into the papillary muscles.
2) Position B: The Impella® catheter is arranged with the pump inlet in the vicinity of the mitral valve apparatus.
3) Position C: The Impella® catheter is positioned deep inside the LV with the pump outlet in the vicinity of the aortic valve leaflets. In each position, the catheter speed is varied 3 times (according to 50%, 75% and 100% of the maximum pump speed). See FIGS. 7-8.

Hemolysis Study

A pair of 2 mL blood samples is collected simultaneously from the distal end of the Swan-Ganz catheter (proximal pulmonary artery) and from the right internal carotid artery sheet after 5 minutes of each phase/position/velocity combination. Complete blood counts (leukocyte, platelet, and erythrocytes) are determined using a hematology analyzer. Total hemoglobin and hematocrit are measured. The plasma-free hemoglobin (pfHb) is calculated by the Harboe direct spectrophotometric method to quantify hemolysis (34). 1 mL aliquots of blood are centrifuged to prepare platelet-poor plasma (PPP). 100 µL PPP is diluted with 1 mL 0.1% Na2CO3 solution (Sigma-Aldrich, St. Louis, MO, USA). Eq. 1 details the calculation of pfHb concentration. Absorbance is measured using a UV/visible spectrophotometer (NanoPhotometer, IMPLEN).

$$pfHb\left(\frac{g}{L}\right) = (167.2 \times A_{415} - 83.6 \times A_{380} - 83.6 \times A_{450}) \times \frac{1}{1000} \times 1/\frac{Vol_{plasma}}{Vol_{Na_2CO_3}} \quad \text{(Eq. 1)}$$

where $A_{415}$ is the sample absorbance at 415 nm, $A_{380}$ is the sample absorbance at 380 nm and $A_{450}$ is sample absorbance at 450 nm. The index of hemolysis (IH) (35) is used to evaluate the experimental data, $$IH(\%) = \frac{\left(1 - \frac{H_{ct}}{100}\right)\frac{pfHb}{1000}}{H_b} \times 100 \quad \text{(Eq. 2)}$$

where $H_{ct}$ is the hematocrit value of the blood expressed in %, pfHb is the concentration of plasma-free hemoglobin (unit: mg/dL), and Hb is the hemoglobin concentration of the whole blood (unit: g/dL). The difference of PFH between the outlet blood sample (carotid artery) and inlet blood sample (pulmonary artery) is used to evaluate shear-induced hemolysis, $IH_{flow}=IH_{outlet}-IH_{inlet}$.

Image Acquisition and Processing

Figure 9:
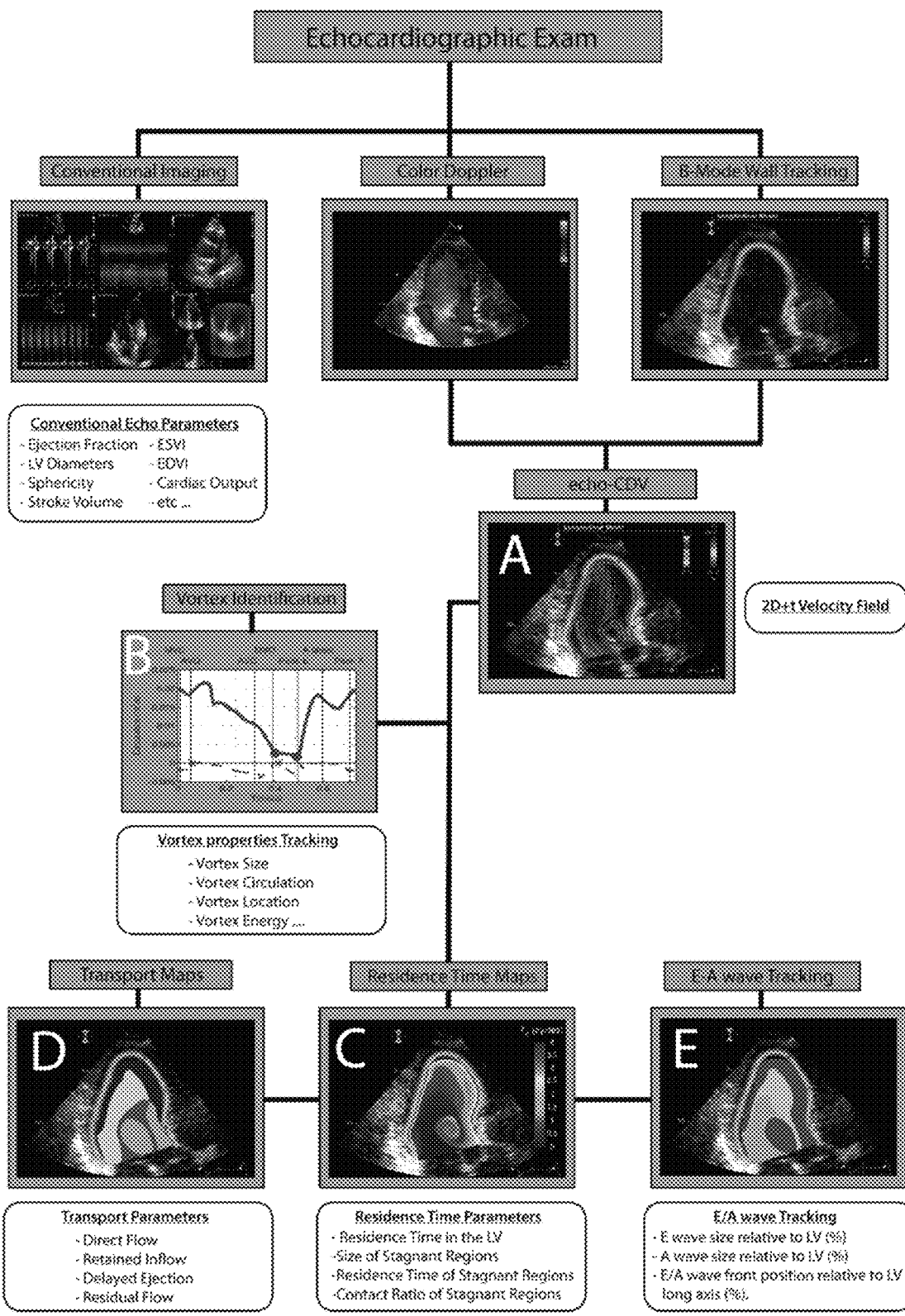
FIG. 9 displays the echocardiographic acquisition and post-processing methodology which include, 2D+t flow reconstruction, intraventricular vortex tracking, blood residence time, transport barriers and E/A wave tracking.
Figure 10:
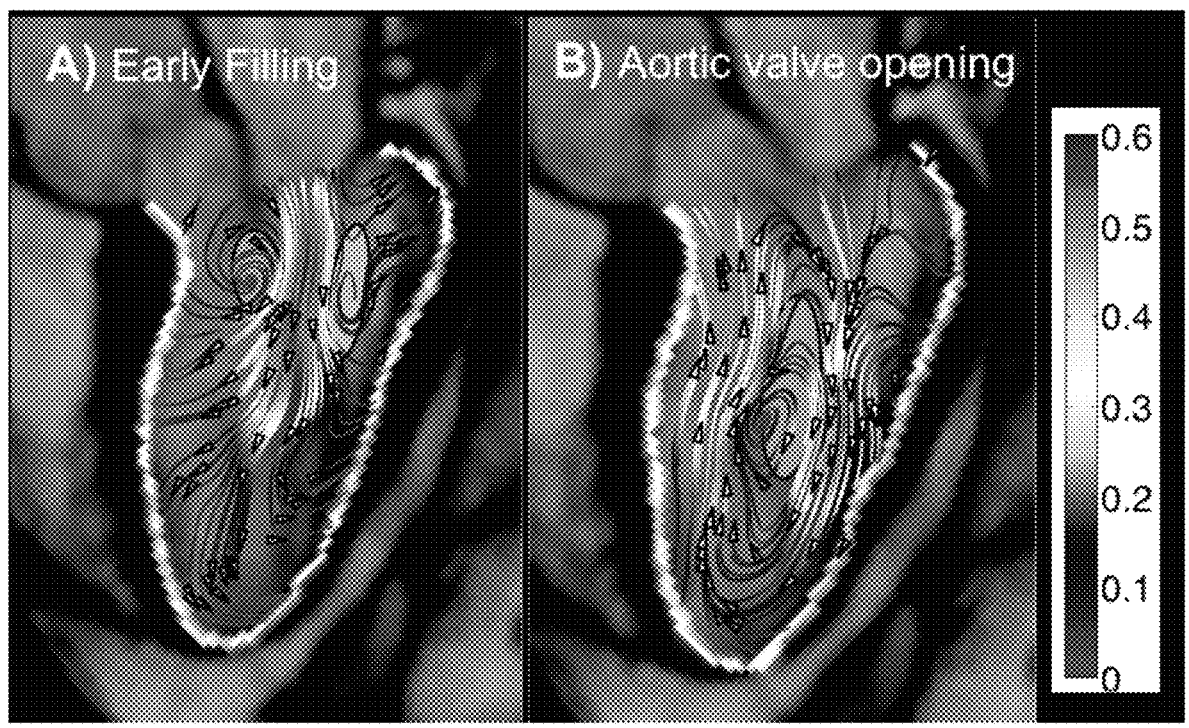
FIG. 10 displays phase contrast MRI blood flow maps in a human left ventricle during early filling (left) and at aortic valve opening (right). Clockwise and counter-clockwise vortices are represented by green and magenta ellipses, respectively.

All the Image acquisition and post-processing methods are depicted in FIG. 9. TTE echocardiographic examinations are performed using a Vivid 7 scanner and phase-array 2-4 MHz transducers (GE Healthcare). Three-dimensional sequences are obtained from apical views to ensure complete apical visualization without foreshortening and are used to measure LV volumes and ejection fractions. Longitudinal, radial and circumferential myocardial strain and strain-rate is measured from apical long-axis and parasternal short axis sequences (EchoPac version 110.1.2, GE Healthcare).

2D+t Flow reconstruction: Color-Doppler velocimetry (Echo-CDV) is used to obtain the unsteady two-dimensional (2D+t) flow field as previously described and validated ((20, 36-38, 39-41), FIG. 9a).

For this purpose, consecutively color-Doppler sequences of 8 to 14 beats are acquired, followed by a 2D cine-loop (4-7 beats) at high frame-rate without moving the probe. Echo-CDV provides the crossbeam flow velocity by integrating the continuity equation, under a planar flow assumption, imposing a condition of non-flow penetration at the myocardium-blood interface.

Figure 6:
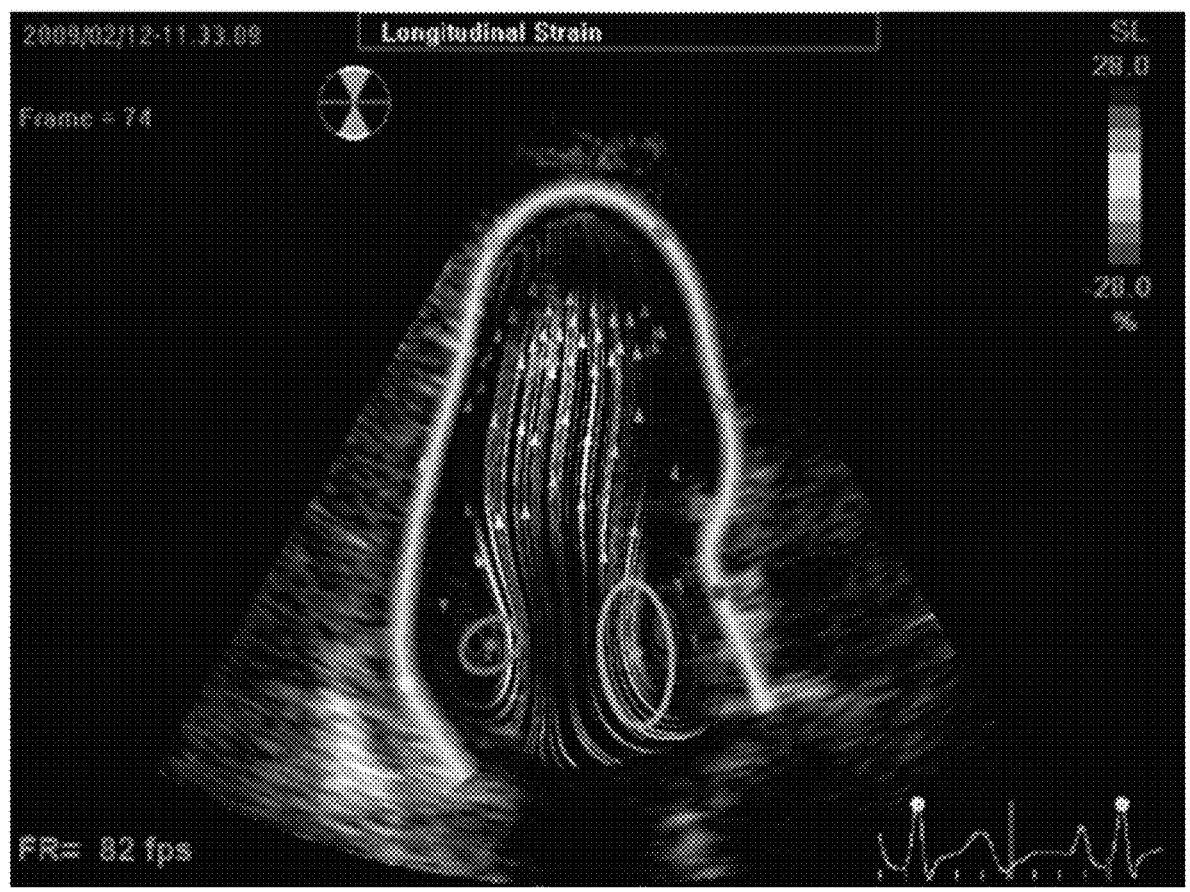
FIG. 6 displays flow in a normal LV at early filling peak obtained suing echo-CDV. The streamline color indicates the velocity magnitude whereas the colored ellipses show the location and size of the intraventricular vortex cores.

Intraventricular Vortex Tracking: In 2-D, the three-dimensional (3-D) LV vortex ring is visualized as two cores corresponding to the intersections between the fluid structure and the imaging plane, with the clockwise rotating section (main) directed toward the anteroseptal wall and the counterclockwise section (secondary) close to the inferolateral LV wall (36, 40) (FIGS. 6 & 9b). Vortex core sections are tracked in a threshold-independent manner using the second invariant of the velocity gradient tensor of the reconstructed 2-D velocity fields, the Q criterion. Time-evolving in-plane properties of the tracked vortex cores are determined from the flow data obtained on the imaging plane. We measure the in-plane circulation, trajectory, kinetic energy density and radius of each core ring. These methods have been widely described by our group (41).

Blood Residence Time: Residence time is defined as the time spent by a blood particle before it leaves the chamber. It has previously been shown that spatio-temporal maps of residence time can be efficiently obtained in the LV from 2D+t echo-CDV data by integrating the equation of advection of a passive scalar with unit forcing (20). This equation is solved for 8 consecutive cardiac cycles to ensure temporal convergence (FIG. 9c). From the residence time maps, the average residence time of the entire blood volume inside the LV is calculated. This is a representative metric of global stasis that accounts for the full blood pool in the ventricle. However, local stasis metrics may be particularly meaningful for mural thrombosis. Therefore, blood regions with a residence time ≥2 s, hereinafter defined as stagnant regions, are also identified and tracked. The following features of the stagnant regions are measured: 1) size relative to total LV volume (area in 2D) (dimensionless), 2) mean residence time inside the region (in cycles), and 3) perimeter of contact of the stagnant region with the endocardium (in % of endocardial length). The contact perimeter of stagnant regions with the endocardium accounts for flow-endocardium interactions that most intensively activate the coagulation cascade (42). Stagnant regions not spanning a full cardiac cycle or <2% of LV area are dismissed.

Transport Barriers: Blood transport volumes are classified as direct flow—blood entering & exiting the LV in the same cardiac cycle—, retained inflow—blood entering in the LV which is not being ejected during the same cycle—, delayed ejection—blood ejected in the studied cycle which entered in the LV during a previous cycle—and residual flow—blood neither entering nor exiting the LV in the studied cycle, therefore spanning in the LV for at least two cardiac cycles—(41, 43-47). From the Residence Time maps (FIG. 9c), we determine the kinetic energy and the size of each transport region in the LV (relative to ventricular volume, area in 2D) at the onset of ejection (FIG. 9d).

E/A wave tracking: To assess the impact of the Impella device on ventricular filling, the residence time maps during diastole are automatically thresholded to separate and track the blood fraction carried by the E and A-waves, and determine the size of these structures and their front location (E/A wave penetration) relative to LV long-axis during the cardiac cycle ((41), FIG. 9e).

Cumulative Blood Shear Stress and Hemolysis: The risk of platelet activation inside the LV is calculated using a power-law model where the stress parameter is the cumulative Von-Mises stress Σ experienced by platelets. is determined H using a forced transport equation, $$\frac{D\sum}{Dt} = \partial_t \sum + (\nabla, \sum) = S; \quad \text{(Eq. 3)}$$

with initial and boundary conditions:

$$H(x, t=0) = 0 \ \& \ H(x_{inlet}, t) = 0; \quad \text{(Eq. 4)}$$

where S is the Von-Mises stress at each point of space and time inside the left ventricle, determined from the velocity field obtained by echo-CDV in each patient.

Statistical Analysis

Experimental data is analyzed using linear mixed-effects models, and paired t-tests where appropriate. The effects of phases, interventions on hemolysis and intraventricular blood transport indices are calculated as the least-mean square estimates and their standard errors. Differences among the different settings are tested using Dunnett's contrasts against baseline measurements. This method is particularly well suited for potentially unbalanced factorial experimental designs as may be expected in the current proposal in the case all experimental factors cannot be replicated in each and every animal.

The association between quantitative variables is assessed by linear mixed-effects models, as well as within-subject correlation coefficients accounting for repeated measures (Rrm) (48). The intraclass regression coefficient ($R_{ic}$) and its 95% confidence interval are used to assess agreement. Variables are described as mean±standard deviation. Statistical analysis is performed using R (49). Values of p<0.05 are considered significant.

Example 3

The success of left ventricular assist device (LVAD) therapy is hampered by complications such as thrombosis, bleeding and right heart failure. Understanding blood flow interactions between the heart and the LVAD will help to optimize treatment and decrease complication rates. It is hypothesized that LVADs, by changing flow patterns, modify shear stresses and blood transit in the left ventricular and that these changes can be characterized using 2D echo color Doppler velocimetry (echo-CDV).

Echo-CDV and custom post-processing methods were used to map and study blood flow inside the LV in patients with ongoing LVAD support (Heartmate II, N=7) and compare it to healthy controls and patients with dilated cardiomyopathy (DCM). Intraventricular flow changes were also analyzed during LVAD ramp tests (baseline±400 rpm).

LVAD support reversed the increase in blood stasis associated to DCM while it did not reduce intraventricular shear exposure. Within the studied range, ventricular flow was largely insensitive to moderate changes in LVAD pump speed. Patients with significant aortic insufficiency showed abnormalities in blood stasis and shear indices.

This Example shows that echocardiography can be used to obtain detailed information about the effect of LVADs on LV flow patterns and blood transit. This technique could potentially be used in combination with standard clinical methods for adjusting LVAD settings in order to optimize flow transport and minimize stasis on an individual basis.

Left ventricular assist device (LVAD) support is a life-saving therapy for patients with advanced heart failure (HF) refractory to optimal medical treatment. The use of LVADs has increased significantly and the treatment is now widely used both as a bridge to heart transplantation and as destination therapy (1, 2). Despite improved survival, major complications such as thrombosis, bleeding and stroke are still common, occurring with an incidence of 8-29% (3-5). The causes of the increased risk of thrombosis in LVAD-implanted patients are multifactorial and not fully understood. Nonetheless, intraventricular flow disturbances leading to abnormal shear stress and blood stasis are recognized as major risk factors (6, 7), and have been associated with thromboembolic strokes (8). Of note, recent studies of patients implanted with new generation LVADs has shown stroke rates comparable to the older generation of devices despite absence of intra-pump thrombosis (5). This observation suggests that the left ventricle (LV) may be a relevant site of local thrombosis and cardioembolism.

The normal LV flow pattern is characterized by a large diastolic vortex that facilitates the transit of blood towards the aorta (9-11), contributing to diastolic transport and reducing kinetic energy losses and cardiac work (12, 13). Moreover, it allows for washing the LV completely in about 2 to 4 beats without inducing shear values high enough to activate platelets (14-16). Devices such as LVADs drastically disrupt the blood flow patterns in the heart and may lead to blood stasis or abnormally large shear stresses (17, 18).

The assessment of intraventricular flow patterns during LVAD treatment has been largely limited to in vitro (19, 20), in silico (21-23) and ex vivo (24) models. These studies have suggested that pump speed, aortic valve opening, cannula location and orientation may be important determinants of intraventricular flow. However, modeling the flow inside the LVAD-assisted ventricle is particularly challenging due to the complex interplays among the pulsatile function of the native myocardium, the continuous LVAD support, and the valves. Consequently, there is a need for in vivo data to quantitatively evaluate intraventricular flow, alterations in stasis and hemodynamic shear in LVAD-implanted patients.

A post-processing method to quantify LV blood stasis and cumulated shear was previously implemented based on clinically applicable echocardiographic color-Doppler velocimetry (echo-CDV) (16, 25-27). An anecdotal application of these methods to an LVAD-implanted patient has been reported (18). Without wishing to be bound by theory, t is hypothesized that echo-CDV could be used to non-invasively characterize the effect of LVAD support in LV hemodynamics and help understand the ventricular-LVAD interplay. Therefore, the present study was designed to characterize the intraventricular flow patterns, as well as to quantify the rates of blood wash-out and shear in the LV in a small sample of patients with Heartmate II LVADs. Flow patterns were compared with data from non-implanted subjects with either normal or dilated LVs. Finally, we assessed the effects of different LVAD pump speeds during ramp tests on intraventricular flow.

Methods

Study Population

Seven subjects undergoing LVAD treatment were prospectively selected from the Heart Failure Clinic at University of California San Diego Sulpizio Cardiovascular Center, in La Jolla, CA. Inclusion criteria for study participants were: 1) the presence of sinus rhythm; 2) a suitable apical ultrasonic window; 3) clinical stability enabling a ramp study, 4) a Doppler signal-to-noise ratio that allowed reliable postprocessing. All LVAD patients had ongoing treatment with a HeartMate II (Thoratec Corp., Pleasanton, Calif.) implanted between 2011-2017 and were examined at a median of 16 (range 3-71) months after implantation.

Twenty normal subjects and twenty patients with non-ischemic dilated cardiomyopathy (DCM) were used as controls. The studies were approved by the corresponding Institutional Review Boards of the two institutions, and all participants provided written informed consent.

Image Acquisition and Analysis

Comprehensive 2-dimensional (2D) B-mode and color-Doppler echocardiographic examinations were performed using Vivid 7 ultrasound scanners and 2-4 MHz phase-array transducers (General Electric Healthcare). Standard 3-chamber view color-Doppler sequences were acquired at each patient's baseline—clinically determined optimal—pump speed, and at 200 rpm increments spanning the range: [baseline−400 rpm] to [baseline+400 rpm]. The total number of acquisitions in the seven patients was 32 (3 acquisitions were discarded due to poor signal-to-noise ratio of the Doppler signal). EchoPac software (version 110.1.2, General Electric Healthcare, Milwaukee, Wis.) was used to delineate the endocardial boundary from the apical long-axis B-mode sequences and a board-certified cardiologist delineated the LVAD cannula on the ventricle wall image using an ad-hoc graphical user interface in MATLAB (Mathworks). The echo-CDV algorithm was then used to calculate time-resolved vector blood velocity maps in the LV, as previously described and validated in vitro (39) and in vivo (36). This algorithm was modified to let blood flow through the cannula (18). Aortic insufficiency (AI) was classified by a board-certified cardiologist and each LVAD patient/speed case was grouped accordingly (absent/mild vs. moderate/severe).

From the reconstructed velocity field, the anteroseptal (clockwise, CW) and inferolateral (counter-clockwise, CCW) sections of the LV vortex ring were identified (36, 40). For each vortex ring section (henceforth referred to as vortex), the circulation, $\Gamma$ (representing the swirling strength), the location along the LV normalized long axis, X ($X=0$ corresponding to the base and $X=1$ to the apex), the radius, R (36), and the ratio between circulation of the CW and CCW vortices were measured. These time-dependent quantities were averaged through the cardiac cycle.

To assess how the interplay between the native pulsatile cardiac function and the constant pump operation affects blood flow pulsatility inside the ventricle, a velocity pulsatility map defined as $$VP(x, y) = T(|v(x, y, t_{max})| - |v(x, y, t_{min})|) / \int_0^T |v(x, y, t)| dt$$

was computed, where T is the cardiac period and |v| is the absolute value of the velocity vector, which reaches its maximum and minimum values at $t_{max}$ and $t_{min}$, respectively. Global chamber flow pulsatility was quantified by the spatial average of VP, denoted as pulsatility index VPI.

The time spent by blood inside the LV (residence time, $T_R$ [s]) was calculated by integrating in time a transport equation (18). In cases with aortic regurgitation, the blood flowing back into the LV was also marked with $T_R=0$, allowing us to segment and track the regurgitant blood volume due to its sharp difference in $T_R$ with respect to blood already present in the LV.

Shear-induced activation of platelets was modeled using a forced advection equation $\partial_t \Sigma + \nabla(v\Sigma) = \gamma (x, y, t)^\alpha$, where $\gamma (x, y, t)$ is a measure of local instantaneous shear rate (50, 51). Based on this equation, a cumulated shear index with dimensions of shear rate as $$CSI = \sum \frac{1}{\alpha - 1}$$

with $\alpha=2$ was defined, based on empirical shear-induced platelet activation data (52). This family of models, with some variations, have been previously used in computational fluid dynamics simulations of shear-mediated hemolysis in LVAD pumps (53).

For the purpose of reporting and comparing data between groups, instantaneous $T_R$ and CSI maps were obtained at the R-wave instant subsequent to 5 seconds of integration ($t=t_{5RW}$). Blood domains with increased residence time ($T_R > 2$ s) were identified and their area ($S_{R, 2s}$) on the imaging plane was computed as a percentage of the LV volume (area in 2D). Likewise, domains with elevated exposure to shear (CSI>200 s$^{-1}$) were identified and their areas ($S_{S, 200/s}$) computed. Global chamber indices of blood stasis and shear exposure were quantified by the spatial maxima and averages of $T_R$ and CSI maps across the whole LV.

Statistical Analysis

Variables were reported as median and interquartile range. After testing for the homogeneity of variance assumption (Levene's test), comparisons among groups were performed using Welch one-way ANOVA test followed by Dunnett-Tukey-Kramer pairwise multiple comparison tests adjusted for unequal variances and sample sizes. Differences in flow indices in the ramp study were analyzed using linear mixed-effects models accounting for repeated measures and described by their fixed effect estimates (β coefficient) and the ANOVA p-value of the model.

Results

The median age of the LVAD group was 74 (interquartile range 64-78) years old. All were males and six of them (86%) had non-ischemic cardiomyopathy. The median age of the DCM group was 62 (IQR 52-72) and all subjects were diagnosed with non-ischemic cardiomyopathy. The healthy control group had a median age of 56 (IQR 53-66). All subjects in the DCM and healthy control groups were males to match LVAD group. Age-matching among groups was not performed due to the advanced age of LVAD group. Echocardiographic and demographic data are reported in Table 1.

TABLE 1

Demographic and echocardiographic data.

|  | Pre-LVAD | LVAD | LVAD | DCM | CONTROL | ANOVA p-value |
|---|---|---|---|---|---|---|
| N | 7 |  | 7 | 20 | 20 |  |
| Age at examination | 74 (62-76) |  | 74 (64-78) | 62 (52-72) | 56 (53-66) | 0.292 |
| Gender (males) |  | 7 (100%) |  | 20 (100%) | 20 (100%) |  |
| Non-ischemic cardiomyopathy |  | 6 (86%) |  | 20 (100%) | 0 (0%) |  |
| Planned destination therapy |  | 3 (43%) |  | — | — |  |
| Device type (HM II) | — |  | 7 (100%) | — | — |  |
| Baseline pump speed (k r.p.m.) | — |  | 9.0 (8.4-9.1) | — | — |  |
| LV EDV (ml) | 284 (220-350) |  | 104 (90-226) | 129 (92-187) | 75 (65-86) $ | 0.0025 |
| LV ESV (ml) | 240 (183-300) |  | 77 (61-160) | 89 (65-131) | 27 (26-32) $ | <0.001 |
| LV EF | 17 (13-22) |  | 28 (24-33) | 28 (23-33) | 63 (59-65) $# | <0.001 |
| HR | 105 (76-117) |  | 68 (61-84) | 61 (58-65) | 60 (56-66) | 0.233 |

HMII, EDV, ESV, EF and HR respectively stand for HeartMate II, end-diastolic volume, end-systolic volume, ejection fraction and heart rate.
Data presented as median (IQR).
$ p < 0.05 vs. LVAD group.
# p < 0.05 between DCM and CONTROL groups.

Blood Flow Patterns

FIG. 11A shows a sequence of instantaneous vector maps and magnitude of LV blood velocity for representative subjects of the LVAD, DCM and normal groups. Continuous suction from the LVAD cannula drives a strong mitral jet that extends all the way from the LV base to the apex and persists throughout the whole cardiac cycle (FIG. 11A, left column). By comparison, in non-treated LVs the filling jet rolls up into a clockwise swirling pattern that redirects blood towards the aortic valve during late diastole and early systole (FIG. 11A, center and right columns).

Quantification of vortex properties (FIG. 11B, Table 2) showed that the main CW vortex was significantly stronger in the LVAD and DCM groups than in the normal group with values of ΓCW=111 (76-148), 99 (73-133), and 60 (38-76) cm2/s, for the LVAD, DCM and normal groups, respectively (p=0.007). The main vortex was also larger and located closer to the apex in DCM and LVAD subjects than in normals [RCW=1.0 (0.9-1.5), 1 (0.7-1.2) and 0.7 (0.5-0.8) cm, p=0.01, XCW=0.4 (0.4-0.4), 0.4 (0.3-0.5) and 0.3

(0.2-0.3), p<0.001]. Due to the more symmetric flow channel created by LVAD support, the secondary CCW vortex was stronger in LVAD than in DCM and normal groups [ΓCCW=43 (25-71), 14 (8-17) and 8 (5-16) cm2/s (p=0.05)].

LV blood flow in LVAD patients was less pulsatile over the cardiac cycle than in the two control groups (FIG. 11D) with values of VPI=1.1 (1.1-1.4), 2.5 (2.2-2.8) and 2.3 (2.1-2.7), p<0.001. Particularly, their velocity pulsatility maps (FIG. 11C) displayed a region of low pulsatility that extended from the mitral valve to the pump cannula and co-localized with the jet induced by cannula suction. In contrast, pulsatility was higher and more uniformly distributed in DCM and normal subjects.

TABLE 2

Flow properties in the three groups

| | | LVAD | DCM | CONTROL | ANOVA P value |
|---|---|---|---|---|---|
| Vortex Circulation (cm²/s) | CCW | 43 (25-71) | 14 (6-17) | 8 (5-16) | |
| | CW | 111 (76-148) | 99 (73-133) | 60 (38-76) [#] | 0.007 |
| Vortices Circulation Ratio (cm²/s) | CCW/CW | 0.4 (0.3-0.6) | 0.1 (0.1-0.2) | 0.1 (0.1-0.3) | 0.02 |
| Vortex Radius (cm) | CCW | 0.4 (0.3-0.8) | 0.3 (0.2-0.4) | 0.2 (0.1-0.3) | |
| | CW | 1 (0.9-1.4) | 1 (0.7-1.2) | 0.7 (0.5-0.8) | 0.01 |
| Vortex Centroid Location (nd) | CCW | 0.3 (0.3-0.5) | 0.3 (0.2-0.4) | 0.3 (0.3-0.4) | |
| | CW | 0.4 (0.4-0.4) | 0.4 (0.3-0.5) | 0.3 (0.2-0.3) [$, #] | <0.001 |
| Pulsatility Index (nd) | | 1.1 (1.1-1.4) | 2.5 (2.2-2.8) [$] | 2.3 (2.1-2.7) [$] | <0.001 |
| Residence Time (sec) | Avg | 0.4 (0.3-0.6) | 1.9 (1.4-2.3) [$] | 1.4 (1.1-1.6) [$] | <0.001 |
| | Max | 2.2 (1.4-2.8) | 5.2 (4.7-5.9) [$] | 5.4 (4.6-6.1) [$] | 0.001 |
| Area of regions with $T_R$ > 2 sec (%) | | 0.1 (0-5.9) | 40.7 (24.6-54.4) [$] | 27.1 (18.1-31.4) | 0.003 |
| CSI (100/s) | Avg | 1.7 (0.9-1.8) | 1.9 (1.5-2.3) | 1.5 (1.4-2.2) | |
| | Max | 6.4 (5-7) | 6 (4.6-7.1) | 5 (3.9-6.7) | |
| Area of regions with CSI > 200/s | | 27.5 (10.6-41.4) | 37.6 (24-49.8) | 32.9 (22.6-39.3) | |

Data presented as median (iqr.).
CCW: Counter clockwise,
CW: Clockwise,
$T_R$: Residence Time,
CSI: Cumulated shear index.
[$] p < 0.05 vs. LVAD group,
[#] p < 0.05 between DCM and CONTROL groups.

Intraventricular Blood Transit and Shear Exposure

Figure 11:
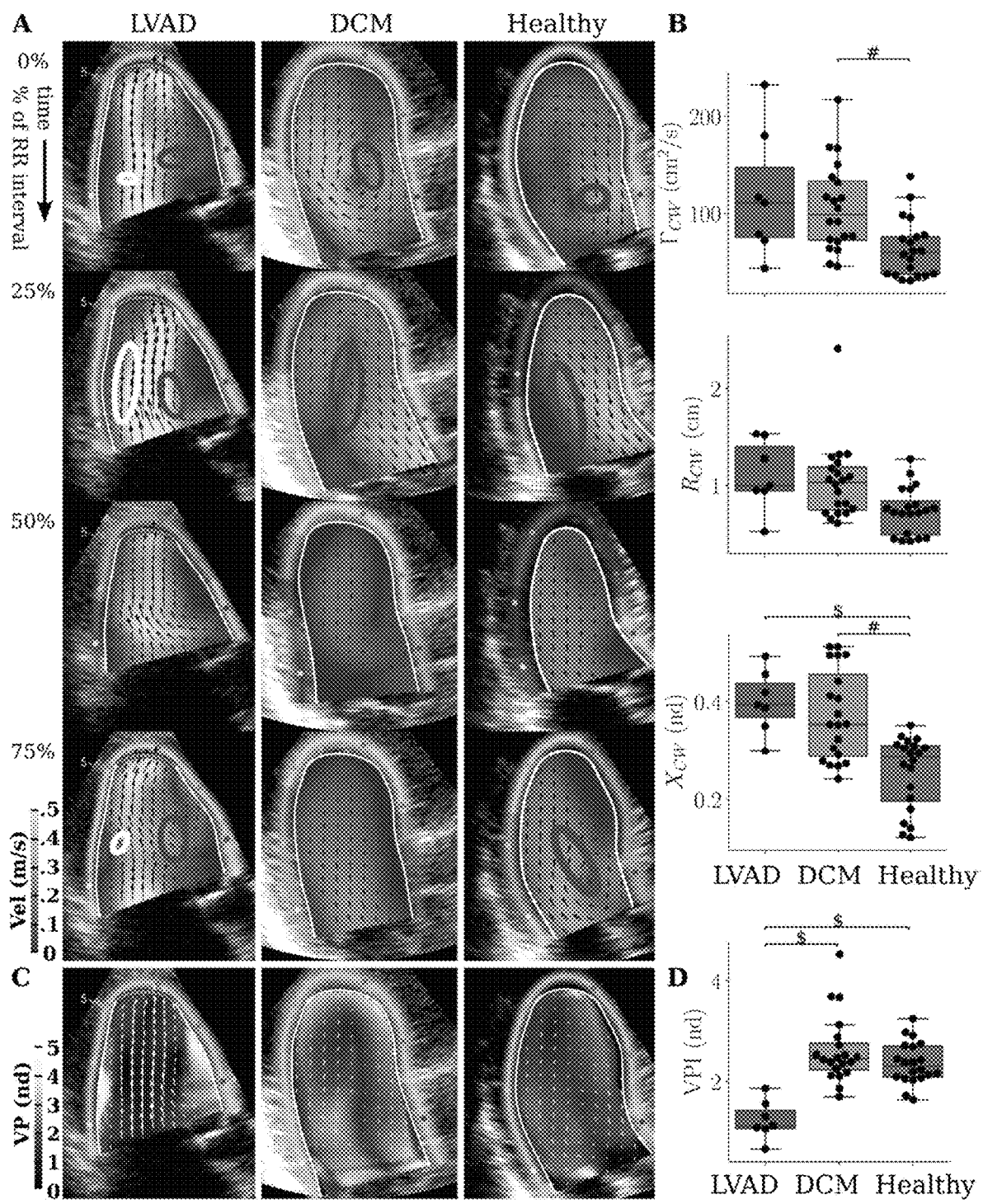
FIG. 11 displays velocity maps and vortex properties. Panel A shows velocity maps with vortices highlighted for a LVAD case (1st column), a dilated cardiomyopathy case (2nd column) and a healthy control case (3rd column) at different time instants within the cardiac cycle (rows as % of RR interval). The blue-green colors and black arrows indicate the instantaneous velocity magnitude and direction. The red (and white) ellipses represent the main clockwise (and secondary counter-clockwise) vortices. Panel B shows boxplots and scatter plots of vortex properties (circulation $\Gamma_{CW}$, radius $R_{CW}$ and longitudinal position $X_{CW}$ of the clockwise main vortex) for patients with LVAD support (blue), dilated cardiomyopathy patients (orange) and healthy controls (green). Panel C shows velocity pulsatility (VP) maps for the same cases of Panel A; white arrows represent the time-averaged velocity field. Panels D shows boxplots and scatter plots of velocity pulsatility index (VPI) for the same groups of Panel B.
Figure 12:
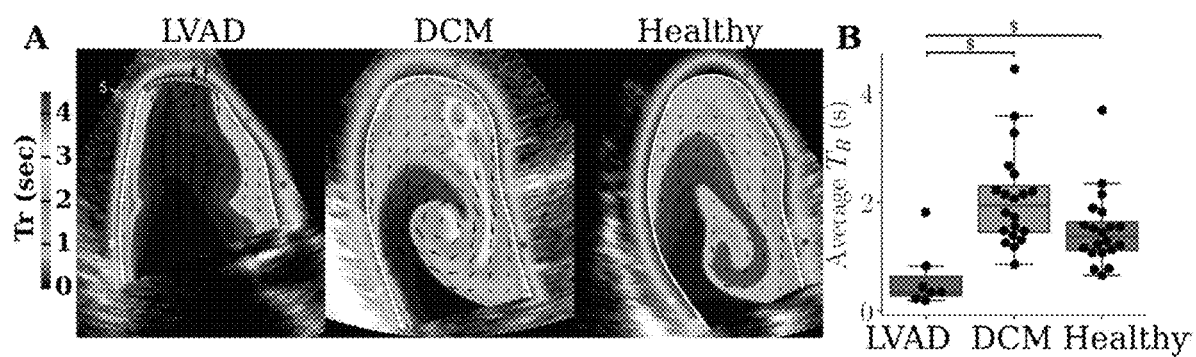
FIG. 12 displays residence time. Panel A shows residence time maps at peak R-wave after 5 seconds of integration for the same cases of FIG. 11A; black arrows indicate the velocity instantaneous magnitude and direction. Panel B shows boxplots and scatter plot of the instantaneous space-averaged residence time at peak R-wave after 5 seconds of integration for the same groups of FIG. 11B.

FIG. 12A displays instantaneous maps of residence time, TR(x, y), for the same representative cases shown in FIG. 11. These maps suggest that suction from the cannula cleared the apical portion of the LV cavity in LVAD subjects. In contrast, non-implanted DCM patients showed large regions of increased residence time that co-localized with the persistent CW diastolic vortex typically found in these patients 15. Consistent with these results, the average LV residence time was lowest in the LVAD group [Average TR=0.4 (0.3-0.6) s, p<0.001], followed by the DCM [1.9 (1.4-2.3) s] and the normal [1.4 (1.1-1.6) s] groups (FIG. 12B & Table 2). Furthermore, LVAD patients had significantly smaller regions with TR>2 seconds than DCM patients and normal controls [SR, 2 s=0.1 (0-5.9), 40.7 (24.6-54.4) and 27.1 (18.1-31.4) %, p=0.003].

Figure 13:
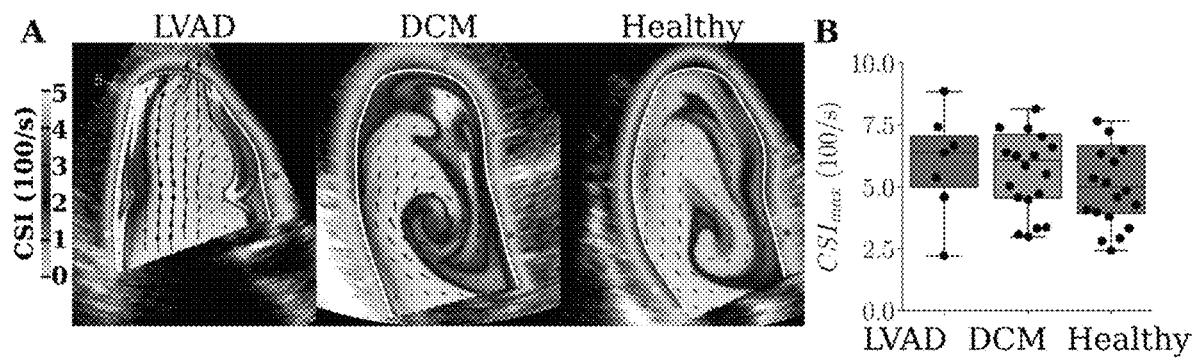
FIG. 13 displays cumulative shear. Panel A shows cumulative shear index (CSI) maps at peak R-wave after 5 seconds of integration for the same cases of FIG. 11A. Panel B shows boxplots and scatter plot of the instantaneous maximum CSI at peak R-wave after 5 seconds of integration for the same groups of FIG. 11B.

Maps of cumulative shear index CSI(x, y, t) are shown in FIG. 13A. In LVAD patients, the basal-to-apical jet driven by cannula suction created continuous shear exposure along the thin edges of the jet (see FIG. 13A). This pattern led to cumulated shear in those regions and low cumulative shear in the core of the jet (FIG. 13B). In non-LVAD the shear exposure had more complex dynamics: it was mostly localized at the edges of the E- and A-waves' filling jets and rolled up driven by the main clockwise LV vortex. Subsequently, the differences in LV washout between the normal and the DCM patients transport had important consequences in terms of cumulated shear. While in normals most of the shear-exposed blood was ejected during systole, a substantial amount of shear-exposed blood could remain trapped in the larger, more persistent vortex of the DCMs (compare central and right panels of FIG. 13A). Overall, LVAD patients had slightly higher maximum values of CSI [CSI max=6.4 (5-7), 6 (4.6-7.1) and 5 (3.9-6.7) s−1] (FIG. 13B & Table 2). The IQRs in Table 2 suggest that the average value cumulative shear in the three groups should range between 90 and 230 s−1 and these data was used to establish CSI>200 s−1 as a threshold for elevated cumulative shear in our study. Based on this threshold, we found that the fraction of LV chamber size occupied by blood with elevated CSI was highest in the DCM cohort and smallest in LVAD patients (FIG. 13C and Table 2).

The Effect of Aortic Insufficiency

Figure 14:
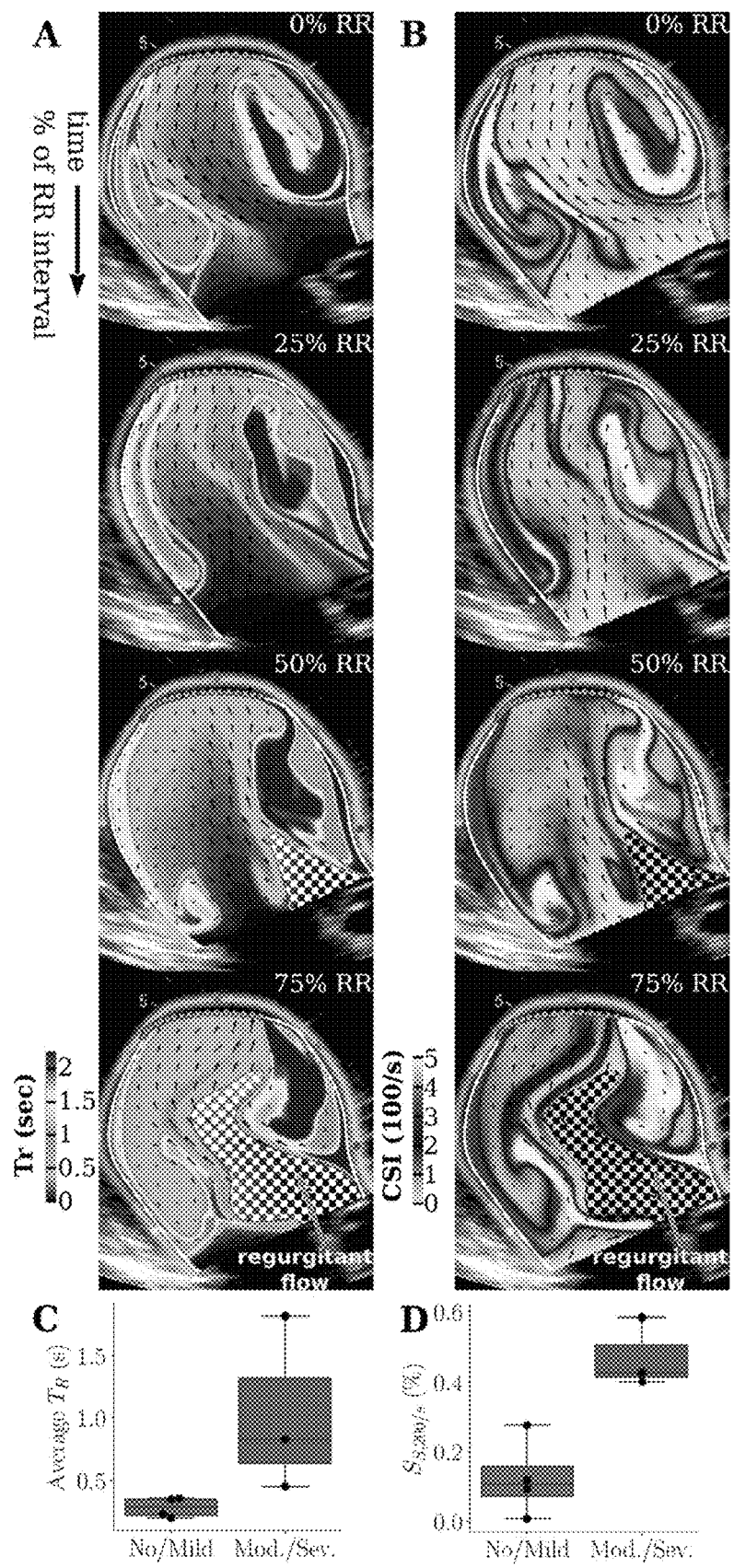
FIG. 14 displays $T_R$ and CSI in LVAD-support with aortic insufficiency. Panel A-B shows residence time maps (A) and cumulative shear index maps (B) for a representative LVAD-implanted patient with severe aortic insufficiency at different time instants within the cardiac cycle (as % of RR interval). The checkered region highlights regurgitant blood entering the LV though the aortic valve. Panel C-D shows boxplots and scatter plots of the space-averaged residence time (C) and size of the high-shear region (CSI>200/s) (D) at peak R-wave after 5 seconds of integration grouped according to the degree of aortic insufficiency.

The relatively wide spread of the data in the LVAD group (see FIGS. 12B and 13C) motivated a more detailed analysis of this group based on aortic insufficiency at baseline pump speed (i.e. AI cohort vs. no-AI cohort). FIG. 14A displays a sequence of maps of TR(x, y) spanning the cardiac cycle for a representative subject of the AI cohort. The plots illustrate how a substantial volume of blood returns to the LV through the aortic valve forming a backflow jet that alternates with the filling jet flowing through the mitral valve. The interaction between these two jets forces intraventricular blood to oscillate back and forth in the chamber, thus impairing LV washout and increasing residence time. This interaction could be enhanced by LVAD support given that cannula suction drives the backflow blood region all the way to the LV apex, as shown in the example case of FIG. 14A. In contrast, AI backflow is observed to remain confined near the LV base in non-implanted patients (data not shown).

Consistent with these observed changes in LV flow patterns, LVAD patients in the AI cohort showed an increase in LV blood average residence time (average TR=0.8 (0.6-1.3) s vs. 0.3 (0.2-0.3) s) and size of the region with TR>2 s (SR, 2 s=11.1 (5.6-30.6)% vs. 0.1 (0.0-0.2)%) compared to the non-AI cohort. Note that these differences were notable even if blood re-entering the LV from the aortic root was tagged with TR=0 seconds as boundary condition, an approximation that likely underestimates the true residence time in the AI cohort. The deficiency in blood clearing observed in the AI cohort also caused shear-exposed blood to remain inside the LV for longer periods of time, allowing for larger regions of elevated cumulative shear to form (e.g. compare the CSI(x, y) map of the AI case in FIG. 14B with the non-AI case of FIG. 13B). Thus, the regions of elevated shear were found to occupy more space the AI cohort than in the non-AI cohort with values of SS, 200=42.6 (41.4-50.5) % and 10.6 (7.2-15.8) %, even if the maximum values of CSI were comparable for the two cohorts. See Table 3 for a summary of residence time and cumulative shear in the AI and non-AI cohorts.

TABLE 3

Residence time and cumulative shear indices for the LVAD patients split in two subsets according to the degree of aortic regurgitation.

|  |  | None-to-Low | Moderate-to Severe |
|---|---|---|---|
| N |  | 4 | 3 |
| Residence Time (sec) | Avg | 0.3 (0.2-0.3) | 0.8 (0.6-1.3) |
|  | Max | 1.6 (1.0-2.2) | 3.4 (2.5-4.2) |
| Size of regions with $T_R > 2$ sec (%) |  | 0.1 (0.0-0.2) | 11.1 (5.6-30.6) |
| CSI (100/s) | Avg | 0.9 (0.8-1.1) | 2.0 (1.9-2.3) |
|  | Max | 5.6 (4.0-7.2) | 6.4 (5.9-6.9) |
| Size of regions with CSI > 200/s |  | 10.6 (7.2-15.8) | 42.6 (41.4-50.5) |

Figure 15:
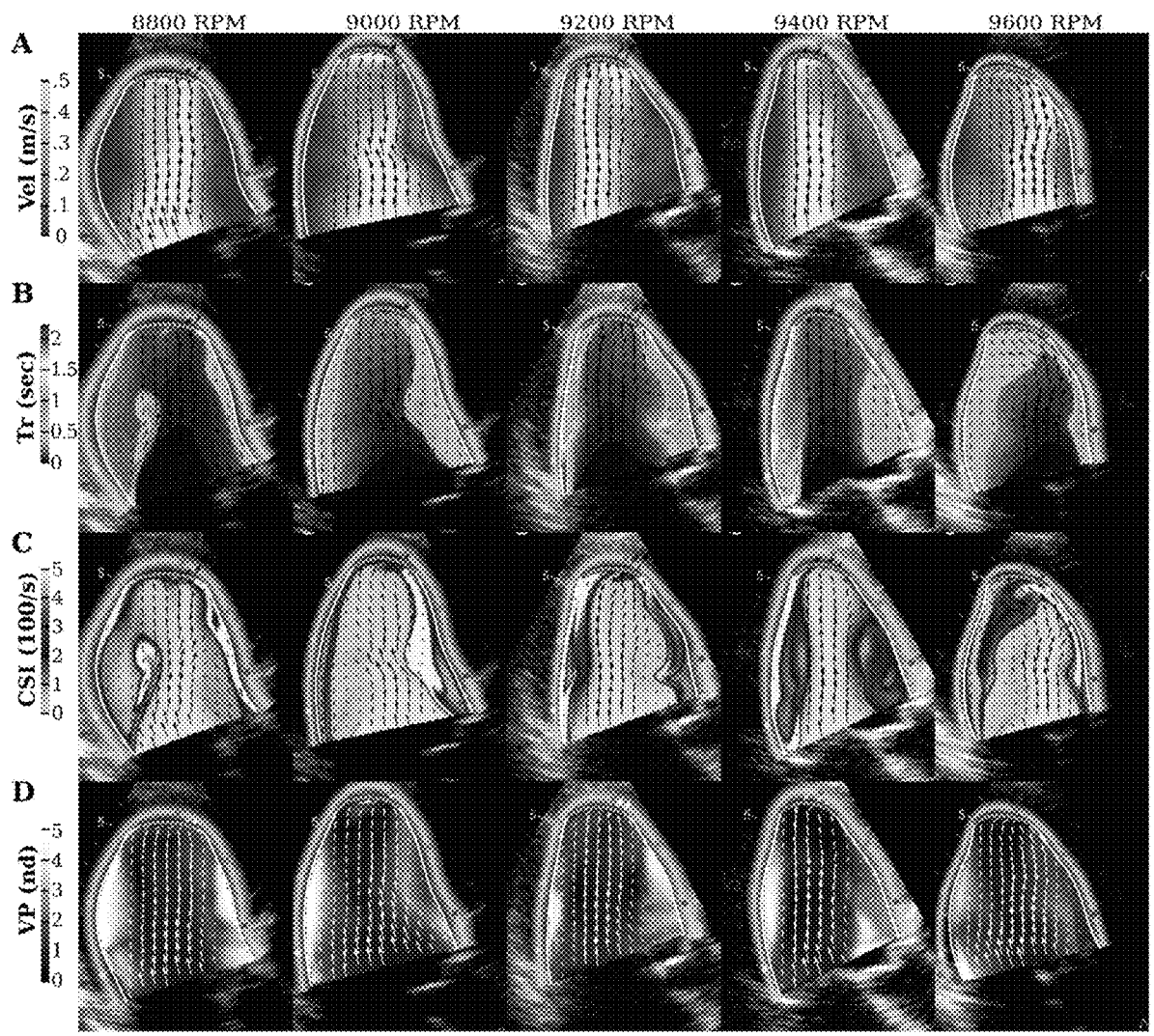
FIG. 15 displays ramp study where velocity (A), residence time (B), cumulative shear index (C) and velocity pulsatility (D) maps for a sample LVAD-implanted patient at different pump speeds (columns) at peak R-wave after 5 seconds of integration.

Data presented as median (iqr).
$T_R$: Residence Time,
CSI: Cumulated shear index Small Variations of LVAD Speed Around Nominal Speed Scarcely Affect LV Flow Patterns Blood flow velocity, pulsatility, residence time and cumulative shear were mapped during ramp studies (FIG. 15) with small LVAD speed changes (each patient's baseline speed±400 rpm). These data suggest that, excepting flow pulsatility, the main features of intraventricular flow in LVAD patients remain almost constant with these pump speed variations. Overall, with increased pump speed a more continuous direct jet between the mitral valve and the LVAD cannula is established, leading to a decrease in pulsatility, but this does not significantly impact global indices of residence time or shear stresses.

Discussion

This Example has quantified how LVAD support affects intraventricular flow patterns, shear stresses and blood transport in a small cohort of axial flow LVAD patients compared to DCM patients and normal controls. Despite the increasingly widespread use of LVADs in advanced HF, the characterization of blood flow inside the LVAD-assisted ventricle has not been well studied and may provide important information to avoid complications after the surgery. These data reveal that, while substantially altering the normal LV flow pattern, LVAD support largely reverses the negative impact of DCM on blood transit through the ventricle. LVAD patients were found to have values of intraventricular residence time that are significantly lower than those of DCM patients and even lower than normals. However, this reduction in residence time did not correspond to a reduction in cumulative blood shear exposure. These data show that these results are relatively independent of LVAD pump speed for small changes around the clinically indicated baseline value whereas blood transit worsened when LVAD support caused moderate or severe aortic insufficiency. These findings provide new insight into blood flow dynamics in the LVAD-supported ventricle and may have important implications for device programming and design.

Left ventricular flow patterns under LVAD support: The hemodynamics of the native LV are dominated by vortices that form during early filling and atrial contraction and evolve into a large clockwise (CW) swirling cell that follows the chiral arrangement of the LV inflow tract (LVIT), the main chamber and the aortic LV outflow tract (LVOT) (9, 10, 33). LVAD-treatment significantly affects these dynamics due to the suction forces created by the pump (34, 35). These data show that LVAD treatment re-routes the transit of blood through the LV so that it forms a straight channel between the LVIT and the LVAD cannula, instead of following a chiral path. The vorticity associated with the boundaries of the jet in LVAD-supported ventricles still results in a pair of vortices. However, consistent with existing in vitro data (19), the net CW rotational motion of blood found in the native LV is reduced by LVAD treatment by stronger counter-CW vortices.

In cases with aortic insufficiency, backflow from the aortic tract formed a counter-CW swirling blood "compartment" that interacted with the natural CW swirling region, creating two separate pockets of blood that rotate inside the LV in alternating directions, and affecting blood residence time and its exposure to shear. Suction from the cannula may accentuate the effects of AI in LVAD patients by driving the aortic backflow close to the LV apex.

The efficiency of re-routing blood transit through the LV: While the native ventricle alternates between reservoir (diastole) and booster (systole) function, LVAD-support forces the ventricle to operate as a conduit. The potential implications of blood re-routing in the total work exerted by the native heart remain debatable after two decades of investigation (10, 13, 14, 33, 36). The implications for platelet activation and thrombosis, which are particularly relevant in LVAD patients, have received less attention. Simulation studies in idealized chamber geometries (13) have shown that the chiral arrangement of the LVIT, the main LV chamber and the LVOT minimize the shear between the filling jet and the intraventricular blood. In contrast, we found that LVAD patients experienced more exposure to shear in the thin layers surrounding the inflow jets than DCM patients and normals.

Flow measurements in LVAD and normal subjects described here suggest that, by establishing a shorter, straighter route for blood transit inside the ventricle, LVAD treatment significantly decreases the LV residence time of blood, but the same trend did not apply to cumulative exposure to shear. It was found that strong persistent vortices in DCM patients can trap blood inside the LV for long times, during which blood is continuously exposed to shear. LVAD treatment causes high instantaneous shear stresses along the edges of the longitudinal jet created by suction at the cannula. However, by improving LV blood transit, it prevents blood from being exposed to increased shear for prolonged periods. When LVAD suction was strong enough to trigger aortic insufficiency the re-routing of blood transit by LVAD treatment was disturbed, becoming less efficient in balancing residence time with blood exposure to shear. These results highlight the need of considering the efficiency of re-routing LV blood transit by jointly assessing blood stasis and cumulative shear as they are tightly interrelated, but do not necessarily vary in the same direction after an intervention. These considerations may be particularly useful for determining the ideal position and angle of the LVAD cannula, which have been suggested to affect LV blood transit (20-23).

Other considerations: The development of in silico and in vitro analyses of intraventricular flow in the LVAD-supported ventricle (19, 21-24) has not been paralleled by a similar surge in pre-clinical or clinical experiments. This lag may in part be due to the inability of performing MRI on LVAD patients. In the current study, the utility of measuring intraventricular flows with ultrasound has been demonstrated. Moreover, it is expected that these new in vivo analyses will facilitate further work to overcome limitations of in vitro and in silico models such as the difficulty of modeling myocardial contraction, relaxation, torsion, valves dynamics, and the physiological response to changes in LVAD support.

The noninvasiveness, portability and device compatibility of echocardiography make this modality well suited for the assessment of intraventricular flow in LVAD patients. In the last decade, several echocardiographic methods have been developed to visualize and quantify blood flow in the left ventricle (37). Particle-image velocimetry applied to contrast ultrasound sequences (echo-PIV) has proven useful and, given that use of contrast agents seems to be safe in patients implanted with third-generation LVADs (38), it is a promising modality to quantify LV flow in these patients. However, this technique requires fine-tuning of the contrast agent infusion (39), which may be particularly challenging in LVAD patients whose pumps destroy contrast agent bubbles (40).

When used in the LV apical long-axis view, echocardiographic color-Doppler velocimetry has good agreement with in silico (41), in vitro (25) and in vivo reference methods (28). Because it imposes free slip boundary conditions at the LV endocardium, it is possible that echo-CDV underestimates endocardial blood shear. Nevertheless, the cumulative shear values obtained here are in good agreement with values measured in vitro with PIV (31).

The LVAD cohort in this pilot study is small and heterogeneous, although most patients had non-ischemic cardiomyopathy (86%) and were >50 years of age (86%). Considering this, the DCM cohort was included as an attempt to control for age and non-ischemic cardiomyopathy.

Clinical implications: LVAD therapy is associated with "hemocompatibility events" such as cerebrovascular accidents, pump thrombosis and hemolysis potentially related to thrombosis inside the ventricle. These complications occur in similar rates in both axial and centrifugal pumps. Currently, there is a lack of clinical tools to guide optimal LVAD settings and cannula placement. Echocardiographic ramp studies are sometimes used to choose pump speeds, but there is limited data showing their utility and no evidence these decrease rates of thromboembolic events. Thrombosis is associated with platelet activation and relative stasis, hemolysis is known to be associated with high shear stress, but currently the risks of these are difficult to estimate in clinical practice and therefore difficult to mitigate. The present data have demonstrated the utility of echo-CDV to evaluate LV hemodynamics in patients with LVADs, and to quantify both LV stasis and shear exposure, which are associated with platelet activation. It was observed that LV stasis was reduced in the group with LVADs compared to the DCM group, while shear was not and pump settings that result in significant aortic insufficiency were associated with a relative increase in stasis and shear exposure. Though AI is a relatively frequent complication of LVAD use (42), an association between AI and thromboembolic events has not been established. Nonetheless, this suggests a potential connection between these two phenomena. In addition, echo-CDV is expected to be useful in guiding LVAD cannula placement and optimal pump settings and therefore decrease the rate of complications and improve outcomes.

REFERENCES FOR EXAMPLE 3

1. Kirklin J K, Pagani F D, Kormos R L, Stevenson L W, Blume E D, Myers S L, Miller M A, Baldwin J T, Young J B, Naftel D C. Eighth annual INTERMACS report: Special focus on framing the impact of adverse events. J Hear Lung Transplant. 2017; 36:1080-1086.
2. Yancy C W, Jessup M, Bozkurt B, Butler J, Casey D E, Colvin M M, Drazner M H, Filippatos G S, Fonarow G C, Givertz M M, Hollenberg S M, Lindenfeld J A, Masoudi F A, McBride P E, Peterson P N, Stevenson L W, Westlake C. 2017 ACC/AHA!HFSA Focused Update of the 2013 ACCF/AHA Guideline for the Management of Heart Failure: A Report of the American College of Cardiology/American Heart Association Task Force on Clinical Practice Guidelines and the Heart Failure Society of Amer. J Am Coll Cardiol. 2017; 70:776-803.
3. Slaughter M S, Rogers J G, Milano C A, Russell S D, Conte J V., Feldman D, Sun B, Tatooles A J, Delgado R M, Long J W, Wozniak T C, Ghumman W, Farrar D J, Frazier O H. Advanced Heart Failure Treated with Continuous-Flow Left Ventricular Assist Device. N Engl J Med. 2009; 361:2241-2251.
4. Rogers J G, Pagani F D, Tatooles A J, Bhat G, Slaughter M S, Birks E J, Boyce S W, Najjar S S, Jeevanandam V, Anderson A S, Gregoric I D, Mallidi H, Leadley K, Aaronson K D, Frazier O H, Milano C A. Intrapericardial Left Ventricular Assist Device for Advanced Heart Failure. N Engl J Med. 2017; 376:451-460.
5. Mehra M R, Naka Y, Uriel N, Goldstein D J, Cleveland J C, Colombo P C, Walsh M N, Milano C A, Patel C B, Jorde U P, Pagani F D, Aaronson K D, Dean D A, McCants K, Itoh A, Ewald G A, Horstmanshof D, Long J W, Salerno C. A Fully Magnetically Levitated Circulatory Pump for Advanced Heart Failure. N Engl J Med. 2017; 376:440-450.
6. Lowe G D O. Virchow's Triad Revisited: Abnormal Flow. Pathophysiol Haemost Thromb. 2003; 33:455-457.
7. Shah P, Birk S, Maltais S, Stulak J, Elmi A, Pagani F D, Cowger J A. Left ventricular assist device outcomes based on flow configuration and pre-operative left ventricular dimension: An Interagency Registry for Mechanically Assisted Circulatory Support Analysis. J Hear Lung Transplant. 2017; 36:640-649.
8. Lip G, Ponikowski P, Andreotti F, Anker S, Filippatos G, Homma S, Morais J, Pullicino P, Rasmussen L, Marin F, Lane D, McMurray J, Hoes A, Ten Berg J, De Caterina R, Kristensen S D, Zeymer U. Thromboembolism and antithrombotic therapy for heart failure in sinus rhythm. Thromb Haemost. 2012; 108:1009-1022.
9. Rodevand O, Bjornerheim R, Edvardsen T, Smiseth O A, Ihlen H. Diastolic Flow Pattern in the Normal Left Ventricle. J Am Soc Echocardiogr. 1999; 12:500-507.
10. Kilner P J, Yang G Z, Wilkes A J, Mohiaddin R H, Firmin D N, Yacoub M H. Asymmetric redirection of flow through the heart. Nature. 2000; 404:759-761.
11. Bolger A, Heiberg E, Karlsson M, Wigström L, Engvall J, Sigfridsson A, Ebbers T, Kvitting J-P E, Carlhäll C J, Wranne B. Transit of Blood Flow Through the Human Left Ventricle Mapped by Cardiovascular Magnetic Resonance. J Cardiovasc Magn Reson. 2007; 9:741-747.
12. Martínez-Legazpi P, Bermejo J, Benito Y, Yotti R, Pérez del Villar C, González-Mansilla A, Barrio A, Villacorta E, Sánchez P L, Fernández-Avilés F, del Álamo J C. Contribution of the Diastolic Vortex Ring to Left Ventricular Filling. J Am Coll Cardiol. 2014; 64:1711-1721.
13. Pedrizzetti G, Domenichini F. Nature optimizes the swirling flow in the human left ventricle. Phys Rev Lett. 2005; 95:108101.
14. Watanabe H, Sugiura S, Hisada T. The looped heart does not save energy by maintaining the momentum of blood flowing in the ventricle. AJP Hear Circ Physiol. 2008; 294:H2191-H2196.

15. Hendabadi S, Bermejo J, Benito Y, Yotti R, Fernández-Avilés F, del Álamo J C, Shadden S C. Topology of Blood Transport in the Human Left Ventricle by Novel Processing of Doppler Echocardiography. Ann Biomed Eng. 2013; 41:2603-2616.
16. Benito Y, Martinez-Legazpi P, Rossini L, Pérez del Villar C, Yotti R, Martin Peinador Y, Rodríguez-Pérez D, Mar Desco M, Medrano C, Antoranz J C, Fernández-Avilés F, del Alamo J C, Bermejo J. Age-dependence of flow homeostasis in the left ventricle. Submitted. 2019.
17. Faludi R, Szulik M, D'hooge J, Herijgers P, Rademakers F, Pedrizzetti G, Voigt J-U. Left ventricular flow patterns in healthy subjects and patients with prosthetic mitral valves: An in vivo study using echocardiographic particle image velocimetry. J Thorac Cardiovasc Surg. 2010; 139:1501-1510.
18. Rossini L, Martinez-Legazpi P, Vu V, Fernández-Friera L, Pérez del Villar C, Rodríguez-López S, Benito Y, Borja M G, Pastor-Escuredo D, Yotti R, Ledesma-Carbayo M J, Kahn A M, Ibáñez B, Fernández-Avilés F, May-Newman K, Bermejo J, del Álamo J C. A clinical method for mapping and quantifying blood stasis in the left ventricle. J Biomech. 2016; 49:2152-2161.
19. Wong K, Samaroo G, Ling I, Dembitsky W, Adamson R, del Álamo J C, May-Newman K. Intraventricular flow patterns and stasis in the LVAD-assisted heart. J Biomech. 2014; 47:1485-1494.
20. Reider C, Moon J, Ramesh V, Montes R, Campos J, Herold B, Martinez-Legazpi P, Rossini L, del Alamo J C, Dembitsky W, May-Newman K. Intraventricular thrombus formation in the LVAD-assisted heart studied in a mock circulatory loop. Meccanica. 2017; 52:515-528.
21. Liao S, Neidlin M, Li Z, Simpson B, Gregory S D. Ventricular flow dynamics with varying LVAD inflow cannula lengths: In-silico evaluation in a multiscale model. J Biomech. 2018; 72:106-115.
22. Prisco A R, Aliseda A, Beckman J A, Mokadam N A, Mahr C, Garcia G J M M. Impact of LVAD Implantation Site on Ventricular Blood Stagnation. ASAIO J. 2017; 63:392-400.
23. Chivukula V K, Beckman J A, Prisco A R, Dardas T, Lin S, Smith J W, Mokadam N A, Aliseda A, Mahr C. Left Ventricular Assist Device Inflow Cannula Angle and Thrombosis Risk. Circ Hear Fail. 2018; 11:e004325.
24. Klotz S, Meyer-Saraei R, Frydrychowicz A, Scharfschwerdt M, Putman L M, Halder S, Sievers H H. Proposing a novel technique to exclude the left ventricle with an assist device: Insights from 4-dimensional flow magnetic resonance imaging. Eur J Cardiothoracic Surg. 2016; 50:439-445.
25. Garcia D, del Alamo J C, Tanné. D, Yotti R, Cortina C, Bertrand É, Antoranz J C, Pérez-David E, Rieu R, Fernández-Avilés F, Bermejo J. Two-dimensional intraventricular flow mapping by digital processing conventional color-doppler echocardiography images. IEEE Trans Med Imaging. 2010; 29:1701-1713.
26. Martinez-Legazpi P, Rossini L, Pérez del Villar C, Benito Y, Devesa-Cordero C, Yotti R, Delgado-Montero A, Gonzalez-Mansilla A, Kahn A M, Fernandez-Avilés F, del Álamo J C, Bermejo J. Stasis Mapping Using Ultrasound. JACC Cardiovasc Imaging. 2018; 11:514-515.
27. Rossini L, Martinez-Legazpi P, Benito Y, Pérez del Villar C, Gonzalez-Mansilla A, Barrio A, Borja M-G, Yotti R, Kahn A M, Shadden S C, Fernández-Avilés F, Bermejo J, del Álamo J C. Clinical assessment of intraventricular blood transport in patients undergoing cardiac resynchronization therapy. Meccanica. 2017; 52:563-576.
28. Bermejo J, Benito Y, Alhama M, Yotti R, Martinez-Legazpi P, del Villar C P, Perez-David E, Gonzalez-Mansilla A, Santa-Marta C, Barrio A, Fernandez-Aviles F, del Alamo J C. Intraventricular vortex properties in nonischemic dilated cardiomyopathy. AJP Hear Circ Physiol. 2014; 306:H718-H729.
29. Hellums J D. 1993 Whitaker lecture: Biorheology in thrombosis research. Ann Biomed Eng. 1994; 22:445-455.
30. Ramstack J M, Zuckerman L, Mockros L F. Shear-induced activation of platelets. J Biomech. 1979; 12:113-125.
31. Vu V, Rossini L, Montes R, Campos J, Moon J, Martinez-Legazpi P, Bermejo J, del Álamo J C, May-Newman K. Mitral Valve Prosthesis Design Affects Hemodynamic Stasis and Shear In The Dilated Left Ventricle. Ann Biomed Eng. 2019. doi:10.1007/s10439-019-02218-z.
32. Fraser K H, Zhang T, Taskin M E, Griffith B P, Wu Z J. A Quantitative Comparison of Mechanical Blood Damage Parameters in Rotary Ventricular Assist Devices: Shear Stress, Exposure Time and Hemolysis Index. J Biomech Eng. 2012; 134:081002.
33. Bermejo J, Martínez-Legazpi P, del Álamo J C. The Clinical Assessment of Intraventricular Flows. Annu Rev Fluid Mech. 2015; 47:315-342.
34. Goodwin M, Nemeh H W, Borgi J, Paone G, Morgan J A. Resolution of Mitral Regurgitation With Left Ventricular Assist Device Support. Ann Thorac Surg. 2017; 104:811-818.
35. Cowger J, Pagani F D, Haft J W, Romano M A, Aaronson K D, Kolias T J. The Development of Aortic Insufficiency in LVAD Supported Patients. Circ Hear Fail. 2015; 3:668-674.
36. Seo J H, Mittal R. Effect of diastolic flow patterns on the function of the left ventricle. Phys Fluids. 2013; 25:110801.
37. Sengupta P P, Pedrizzetti G, Kilner P J, Kheradvar A, Ebbers T, Tonti G, Fraser A G, Narula J. Emerging Trends in CV Flow Visualization. JACC Cardiovasc Imaging. 2012; 5:305-316.
38. Schinkel A F L, Akin S, Strachinaru M, Muslem R, Soliman O I I, Brugts J J, Constantinescu A A, Manintveld O C, Caliskan K. Safety and feasibility of contrast echocardiography for the evaluation of patients with HeartMate 3 left ventricular assist devices. Eur Heart J Cardiovasc Imaging. 2018; 19:690-693.
39. Gao H, Claus P, Amzulescu M S, Stankovic I, D'Hooge J, Voigt J U. How to optimize intracardiac blood flow tracking by echocardiographic particle image velocimetry? Exploring the influence of data acquisition using computer-generated data sets. Eur Heart J Cardiovasc Imaging. 2012; 13:490-499.
40. Platts D G, Bartnikowski N, Gregory S D, Scalia G M, Fraser J F. Contrast Microsphere Destruction by a Continuous Flow Ventricular Assist Device: An In Vitro Evaluation Using a Mock Circulation Loop. Biomed Res Int. 2017; 2017:1-9.

41. Uejima T, Koike A, Sawada H, Aizawa T, Ohtsuki S, Tanaka M, Furukawa T, Fraser A G. A new echocardiographic method for identifying vortex flow in the left ventricle: Numerical validation. Ultrasound Med Biol. 2010; 36:772-788.

42. Jorde U P, Uriel N, Nahumi N, Bejar D, Gonzalez-Costello J, Thomas S S, Han J, Morrison K A, Jones S, Kodali S, Hahn R T, Shames S, Yuzefpolskaya M, Colombo P, Takayama H, Naka Y. Prevalence, significance, and management of aortic insufficiency in continuous flow left ventricular assist device recipients. Circ Hear Fail. 2014; 7:310-319.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. Indeed, various modifications of the invention in addition to those described herein will become apparent to those skilled in the art from the foregoing description and the accompanying figures. Such modifications are intended to fall within the scope of the appended claims It is further to be understood that all values are approximate, and are provided for description. Patents, patent applications, publications, product descriptions, and protocols are cited throughout this application, the disclosures of which are incorporated herein by reference in their entireties for all purposes.

What is claimed is:

1. A method performed by one or more computers, the method comprising:
   obtaining a plurality of flow-velocity images of blood inside a cardiac chamber or blood vessel of a subject;
   processing the plurality of flow-velocity images to generate a Von-Mises stress map, wherein the Von-Mises stress map defines a respective amount of Von-Mises stress experienced by blood particles at each of a plurality of time points and at each of a plurality of spatial positions inside the cardiac chamber or blood vessel;
   processing the plurality of flow-velocity images to generate a residence time map, wherein the residence time map defines a respective residence time of blood particles at each of a plurality of spatial positions inside the cardiac chamber or blood vessel;
   generating a cumulative fluid shear stress map as a function of the Von-Mises stress map using a transport equation, wherein the cumulative fluid shear stress map defines a respective cumulative amount of fluid shear stress experienced by blood particles at each of a plurality of spatial positions inside the cardiac chamber or blood vessel over the plurality of time points; and
   processing: (i) the cumulative fluid shear stress map, and (ii) the residence time map, to identify one or more regions of hemolysis inside the cardiac chamber or blood vessel.

2. The method of claim 1, wherein processing the plurality of flow-velocity images to generate the Von-Mises stress map comprises:
   processing the plurality of flow-velocity images to generate a velocity map, wherein the velocity map defines a respective velocity of blood particles at each of a plurality of spatial positions inside the cardiac chamber or blood vessel; and
   processing the velocity map to generate the Von-Mises stress map.

3. The method of claim 1, wherein generating the cumulative fluid shear stress map as a function of the Von-Mises stress map using the transport equation comprises:
   numerically integrating the Von-Mises stress map over time.

4. The method of claim 1, wherein identifying the one or more regions of hemolysis based on both: (i) the cumulative fluid shear stress map, and (ii) the residence time map, comprises:
   determining, for each of a plurality of spatial positions inside the cardiac chamber or blood vessel, a product of: (i) a first value derived from evaluating the cumulative fluid shear stress map at the spatial position, and (ii) a second value derived from evaluating the residence time map at the spatial position.

5. The method of claim 1, further comprising processing the cumulative fluid shear stress map to identify a region where cumulative fluid shear stress on blood particles inside the region exceeds a threshold.

6. The method of claim 5, further comprising determining a fraction of a volume of the cardiac chamber or blood vessel that is occupied by the region where the cumulative fluid shear stress on blood particles inside the region exceeds the threshold.

7. The method of claim 1, wherein the subject has an implanted electromechanical device.

8. The method of claim 7, wherein the implanted electromechanical device is a ventricular assist device.

9. The method of claim 8, wherein the ventricular assist device is a left ventricular assist device.

10. The method of claim 1, wherein the cardiac chamber is a left ventricular cardiac chamber.

11. The method of claim 1, wherein the subject is a human, a monkey, a dog, a cat, a horse, a pig, a rat, or a mouse.

12. The method of claim 1, wherein each one of the plurality of flow-velocity images are two-dimensional or three-dimensional flow-velocity images.

13. The method of claim 1, wherein each of the plurality of flow-velocity images are acquired by an echocardiogram apparatus.

14. The method of claim 1, wherein each of the plurality of flow-velocity images are acquired by a magnetic resonance imaging apparatus.

15. The method of claim 1, wherein each of the plurality of flow-velocity images are acquired by a color-Doppler velocimetry apparatus.

16. The method of claim 1, wherein each of the plurality of flow-velocity images are acquired by a synthetic aperture ultrasound apparatus.

17. A system comprising:
   one or more computers; and
   one or more storage devices communicatively coupled to the one or more computers, wherein the one or more storage devices store instructions that, when executed by the one or more computers, cause the one or more computers to perform operations comprising:
      obtaining a plurality of flow-velocity images of blood inside a cardiac chamber or blood vessel of a subject;
      processing the plurality of one or more flow-velocity images to generate a Von-Mises stress map, wherein the Von-Mises stress map defines a respective amount of Von-Mises stress experienced by blood particles at each of a plurality of time points and at each of a plurality of spatial positions inside the cardiac chamber or blood vessel;

processing the plurality of flow-velocity images to generate a residence time map, wherein the residence time map defines a respective residence time of blood particles at each of a plurality of spatial positions inside the cardiac chamber or blood vessel;

generating a cumulative fluid shear stress map as a function of the Von-Mises stress map using a transport equation, wherein the cumulative fluid shear stress map defines a respective cumulative amount of fluid shear stress experienced by blood particles at each of a plurality of spatial positions inside the cardiac chamber or blood vessel over the plurality of time points; and processing: (i) the cumulative fluid shear stress map, and (ii) the residence time map, to identify one or more regions of hemolysis inside the cardiac chamber or blood vessel.

18. One or more non-transitory computer storage media storing instructions that when executed by one or more computers cause the one or more computers to perform operations comprising:

obtaining a plurality of flow-velocity images of blood inside a cardiac chamber or blood vessel of a subject;

processing the plurality of flow-velocity images to generate a Von-Mises stress map, wherein the Von-Mises stress map defines a respective amount of Von-Mises stress experienced by blood particles at each of a plurality of time points and at each of a plurality of spatial positions inside the cardiac chamber or blood vessel;

processing the plurality of flow-velocity images to generate a residence time map, wherein the residence time map defines a respective residence time of blood particles at each of a plurality of spatial positions inside the cardiac chamber or blood vessel;

generating a cumulative fluid shear stress map as a function of the Von-Mises stress map using a transport equation, wherein the cumulative fluid shear stress map defines a respective cumulative amount of fluid shear stress experienced by blood particles at each of a plurality of spatial positions inside the cardiac chamber or blood vessel over the plurality of time points; and processing: (i) the cumulative fluid shear stress map, and (ii) the residence time map, to identify one or more regions of hemolysis inside the cardiac chamber or blood vessel.

19. The non-transitory computer storage media of claim 18, wherein processing the plurality of flow-velocity images to generate the Von-Mises stress map comprises:

processing the plurality of flow-velocity images to generate a velocity map, wherein the velocity map defines a respective velocity of blood particles at each of a plurality of spatial positions inside the cardiac chamber or blood vessel; and processing the velocity map to generate the Von-Mises stress map.

20. The non-transitory computer storage media of claim 18, wherein generating the cumulative fluid shear stress map as a function of the Von-Mises stress map using the transport equation comprises:

numerically integrating the Von-Mises stress map over time.

* * * * *

UNITED STATES PATENT AND TRADEMARK OFFICE
CERTIFICATE OF CORRECTION

| | | |
|---|---|---|
| PATENT NO. | : 12,257,072 B2 | Page 1 of 1 |
| APPLICATION NO. | : 17/955077 | |
| DATED | : March 25, 2025 | |
| INVENTOR(S) | : Juan Carlos del Alamo de Pedro et al. | |

It is certified that error appears in the above-identified patent and that said Letters Patent is hereby corrected as shown below:

On the Title Page

Column 1 (under Applicant), Line 2, delete "California;" insert -- California Oakland, CA (US); --.

In the Claims

Column 42, Line 65, in Claim 17, after "of" delete "one or more".

Signed and Sealed this
Twenty-seventh Day of May, 2025

Coke Morgan Stewart
*Acting Director of the United States Patent and Trademark Office*